(12) United States Patent
Zhang

(10) Patent No.: US 8,865,402 B2
(45) Date of Patent: Oct. 21, 2014

(54) NANOSTRUCTURED SUBSTRATES FOR SURFACE ENHANCED RAMAN SPECTROSCOPY (SERS) AND DETECTION OF BIOLOGICAL AND CHEMICAL ANALYTES BY ELECTRICAL DOUBLE LAYER (EDL) CAPACITANCE

(75) Inventor: Guigen Zhang, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 449 days.

(21) Appl. No.: 12/869,504

(22) Filed: Aug. 26, 2010

(65) Prior Publication Data

US 2011/0053794 A1 Mar. 3, 2011

Related U.S. Application Data

(60) Provisional application No. 61/237,034, filed on Aug. 26, 2009, provisional application No. 61/310,875, filed on Mar. 5, 2010.

(51) Int. Cl.

| | | |
|---|---|---|
| *C12Q 1/68* | (2006.01) | |
| *C12M 1/36* | (2006.01) | |
| *G01N 27/00* | (2006.01) | |
| *B01J 19/00* | (2006.01) | |
| *G01N 33/543* | (2006.01) | |
| *G01N 21/65* | (2006.01) | |
| *B82Y 30/00* | (2011.01) | |
| *B82Y 40/00* | (2011.01) | |
| *G01N 33/553* | (2006.01) | |

(52) U.S. Cl.

CPC ... *G01N 33/5438* (2013.01); *B01J 2219/00704* (2013.01); *B01J 2219/00585* (2013.01); *B01J 19/0046* (2013.01); *B01J 2219/00533* (2013.01); *B01J 2219/00596* (2013.01); *G01N 21/658* (2013.01); *B01J 2219/00605* (2013.01); *B01J 2219/00509* (2013.01); *B82Y 30/00* (2013.01); *B82Y 40/00* (2013.01); *G01N 33/553* (2013.01); *B01J 2219/00659* (2013.01); *B01J 2219/00653* (2013.01)

USPC .................. 435/6.1; 435/287.2; 422/82.01

(58) Field of Classification Search
None
See application file for complete search history.

(56) References Cited

U.S. PATENT DOCUMENTS

2006/0038990 A1* 2/2006 Habib et al. ................ 356/301
2007/0274895 A1* 11/2007 Jesih et al. ................. 423/462

(Continued)

OTHER PUBLICATIONS

Anandan et al. "Nanopillar array structures for enhancing biosensing performance", *Int. J. Nanomedicine* 1(1):73-79 (2006).

(Continued)

*Primary Examiner* — Betty Forman
(74) *Attorney, Agent, or Firm* — Myers Bigel Sibley & Sajovec, P.A.

(57) ABSTRACT

Provided according to embodiments of the invention are nanostructured surfaces that include a substrate; and an array of metallic nanopillar islands on the substrate, wherein each metallic nanopillar island includes a metal base layer on the substrate and a plurality of metallic nanopillars on the metal base layer, and wherein portions of the substrate between adjacent metallic nanopillar islands are free of the metal base layer. Also provided according to some embodiments of the invention are nanostructured surfaces that include a non-conductive substrate; and at least one nanoelectrode defined within the non-conductive substrate, wherein the at least one nanoelectrode is sized and/or shaped to immobilize an analyte or a probe molecule. Also provided are apparatuses and methods for SERS and detection of analytes or biological binding by EDL capacitance.

18 Claims, 19 Drawing Sheets

(56) References Cited

U.S. PATENT DOCUMENTS

| | | | |
|---|---|---|---|
| 2008/0174775 A1* | 7/2008 | Moskovits et al. | 356/301 |
| 2009/0146081 A1* | 6/2009 | Stark | 250/492.2 |
| 2009/0243584 A1 | 10/2009 | Zhang et al. | |
| 2009/0297913 A1 | 12/2009 | Zhang et al. | |
| 2010/0066346 A1 | 3/2010 | Zhang et al. | |

OTHER PUBLICATIONS

Lee et al. "Hot Spots in Silver Nanowire Bundles for Surface-Enhanced Raman Spectroscopy", *J. Am. Chem. Soc.* 128:2200-2201 (2006).

Anandan et al. "Role of reaction kinetics and mass transport in glucose sensing with nanopillar array electrodes", *Journal of Biological Engineering*:1-10 (Oct. 10, 2007).

Branton et al. "The potential and challenges of nanopore sequencing", *Nature Biotechnology* 26(10):1146-1153 (2008).

Coombs "The sequencing shakeup", *Nature Biotechnology* 26(10):1109-1112 (2008).

Grahame "The Electrical Double Layer and the Theory of Electrocapillarity", *Chem. Rev.* 41:441-501 (1947).

He et al. "Identification of DNA Basepairing via Tunnel-Current Decay", *Nano Letters* 7(12):3854-3858 (2007).

Heng et al. "Beyond the Gene Chip", *Bell Labs Tech. Journal* 10(3):5-22 (2005).

Ho et al. "Electrolytic transport through a synthetic nanometer-diameter pore", *Pnas* 102(30):10445-10450 (2005).

Kolb "Electrochemical Surface Science", *Angew. Chem. Int. Ed.* 40:1162-1181 (2001).

Lagerqvist et al. "Influence of the Environment and Probes on Rapid DNA Sequencing via Transverse Electronic Transport", *Biophysical Journal* 93:2384-2390 (2007).

Lin et al. "Nanopillar Subtrate for SERS", 7th International Conference on Miniaturized Chemical and Biochemical Analysis Systems 705-708 (Oct. 5-9, 2003).

Masuda et al. "Ordered Metal Nanohole Arrays Made by a Two-Step Replication of Honeycomb Structures of Anodic Alumina", *Science* 268:1466-1468 (1995).

Masuda et al. "Self-repair of ordered pattern of nanometer dimensions based on self-compensation properties of anodic porous alumina", *Applied Physics Letters* 78(6):826-828 (2001).

Parry et al. "In Situ Fourier Transform Infrared Spectroelectrochemical Study of Bisulfate and Sulfate Adsorption on Gold, with and without the Underpotential Deposition of Copper", *Langmuir* 9:1878-1887 (1993).

Singhal et al. "Ultrasensitive Voltammetric Detection of Underivatized Oligonucleotides and DNA", *Anal. Chem.* 69:4828-4832 (1997).

Yang et al. "Simulating the structure and effect of the electrical double layer at nanometer electrodes", *Nanotechnology* 18:1-9 2007.

Yang et al. "The effect of an electrical double layer on the voltammetric performance of nanoscale interdigitated electrodes: a simulation study", *Nanotechnology* 19:1-8 (2008).

Moustafa et al. "Electrodeposition of Al in 1-Butyl-1-methylpyrrolidinium Bis(trifluoromethylsulfonyl)amide and 1-Ethyl-3-methylinnidazolium Bis(trifluoromethylsulfonyl)amide Ionic Liquids: In Situ STM and EQCM Studies", *J. Phys. Chem. B*. 111:4693-4704 (2007).

Rao et al. "Fast Fourier Transform Analysis of Pore Pattern in Anodized Alumina Formed at Various Conditions", *J. Nanosci. Nanotechnol.* 5(12):2070-2075 (2005).

U.S. Appl. No. 12/777,377, filed May 11, 2010, Zhang.

* cited by examiner

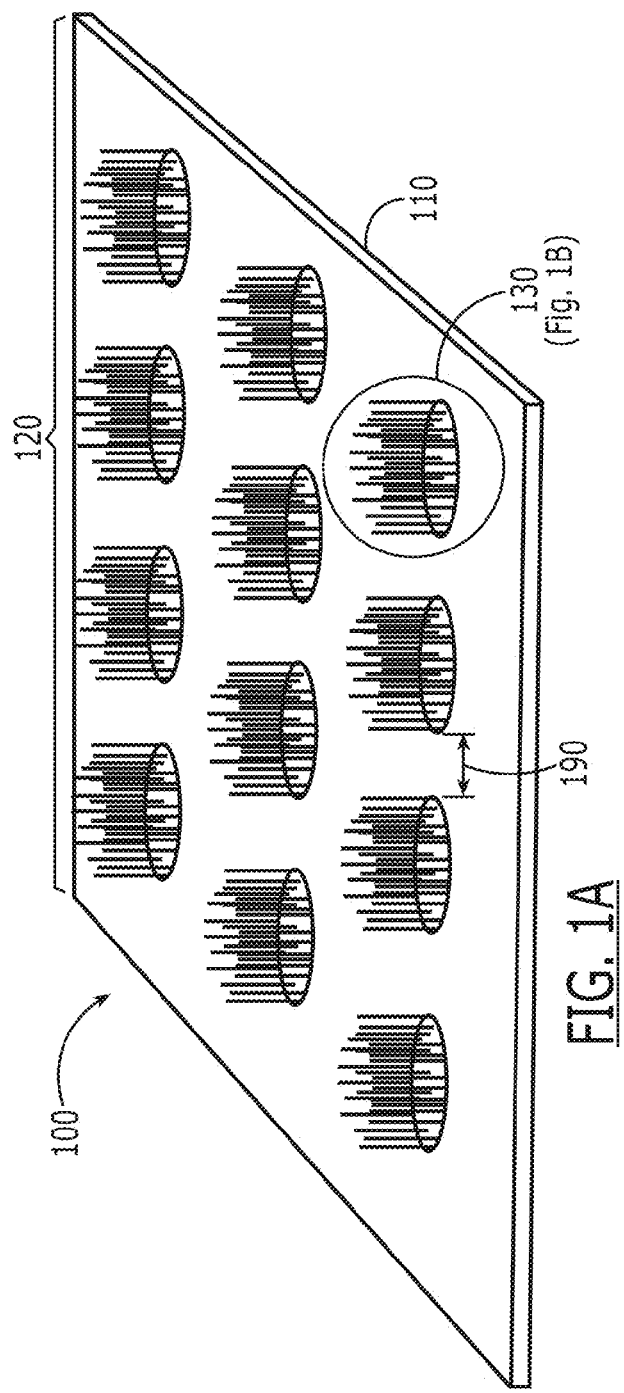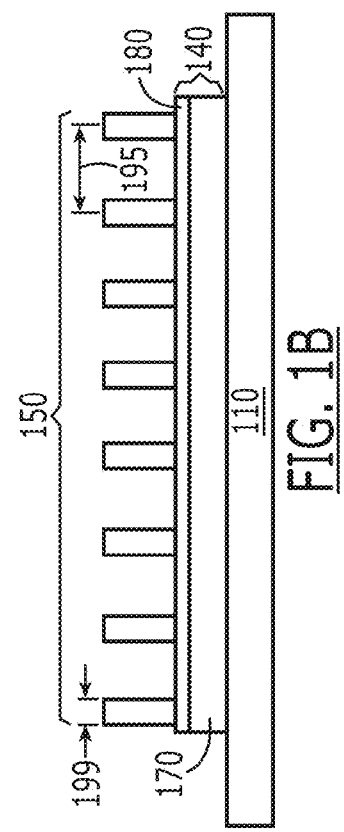

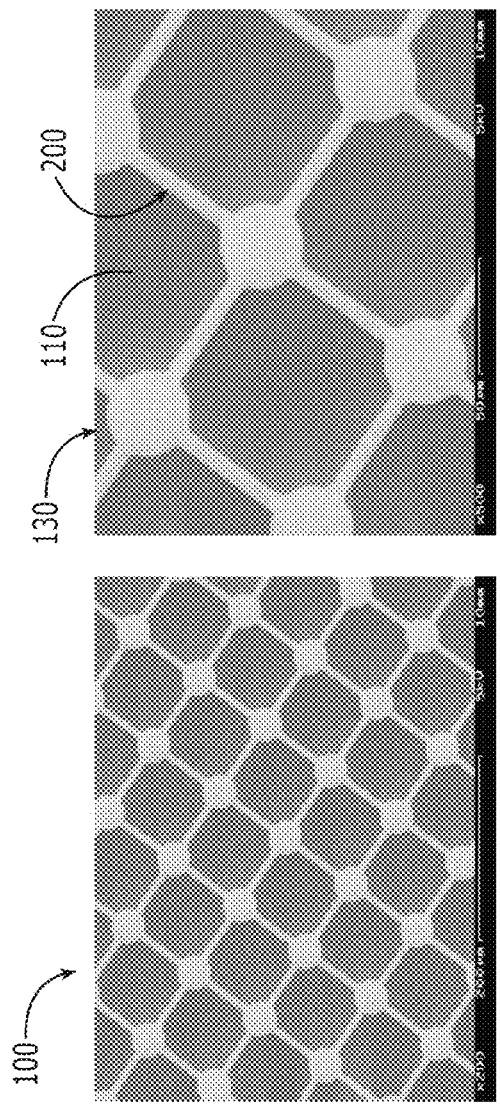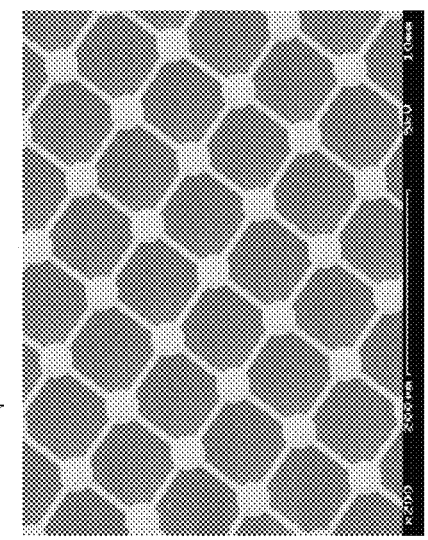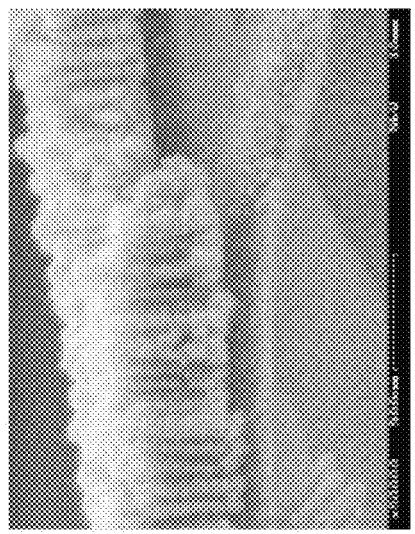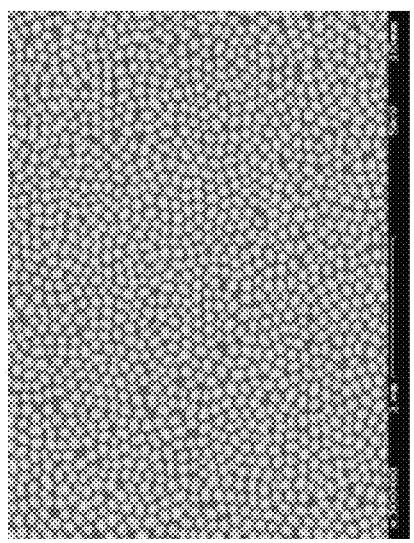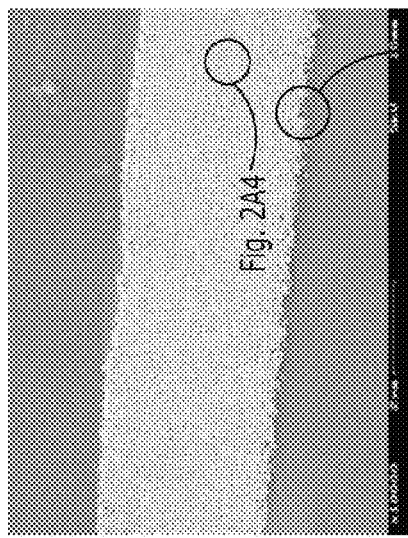
FIG. 2A1
FIG. 2A2
FIG. 2A3
FIG. 2A4
FIG. 2A5

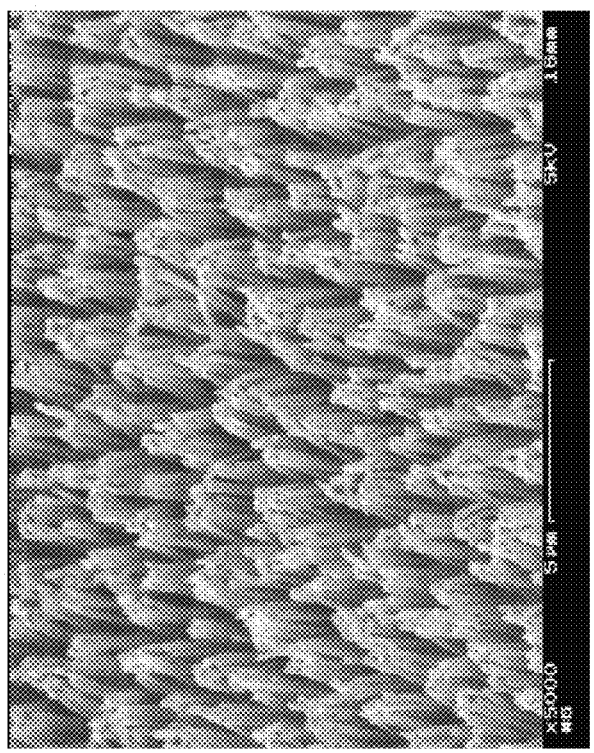
FIG. 2B2
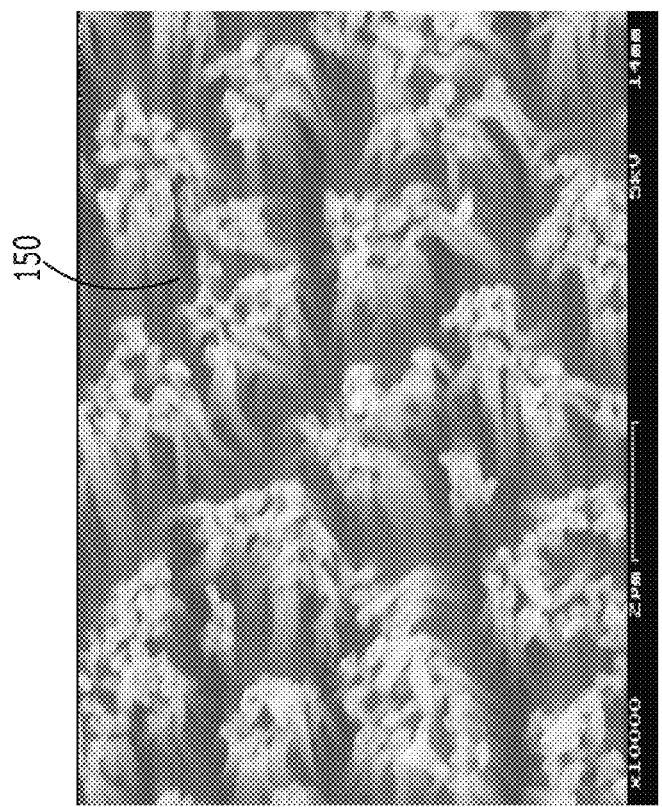
FIG. 2B1

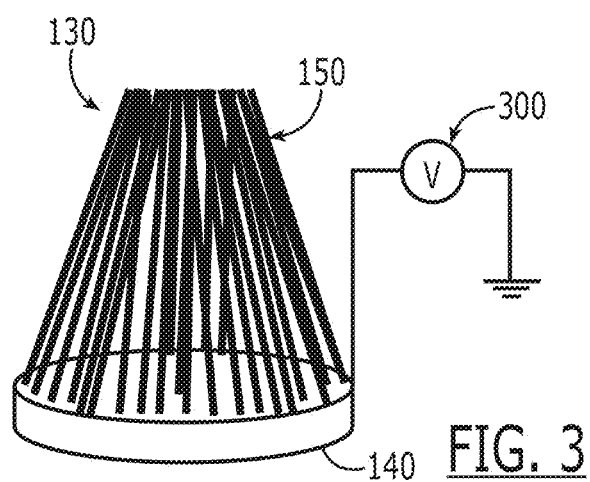

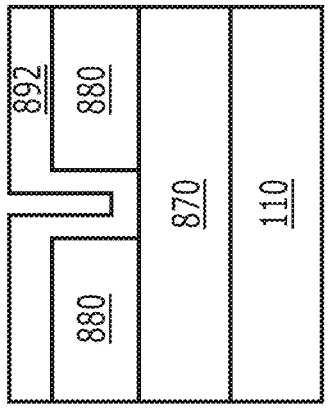# FIG. 8B1
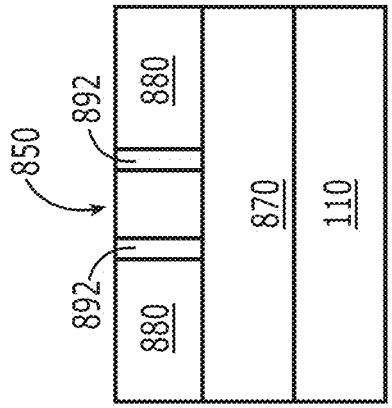# FIG. 8B2
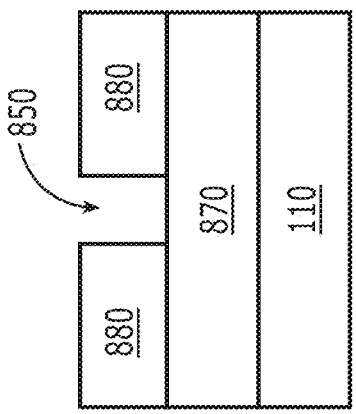# FIG. 8B3
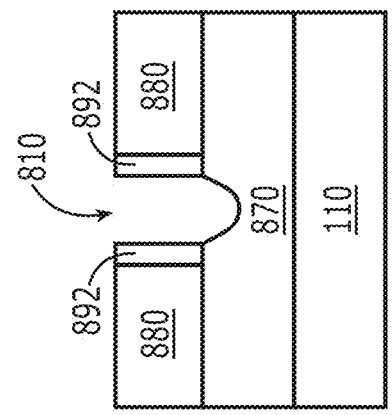# FIG. 8C1
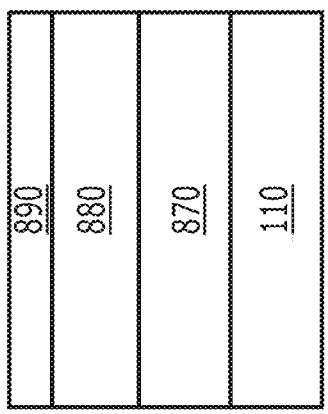# FIG. 8C2
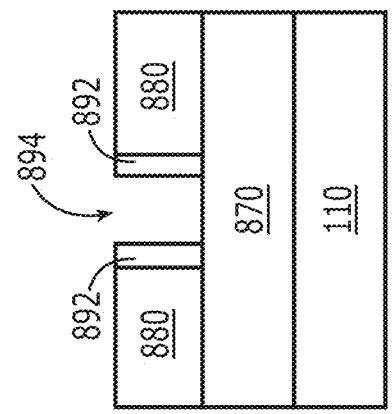# FIG. 8C3

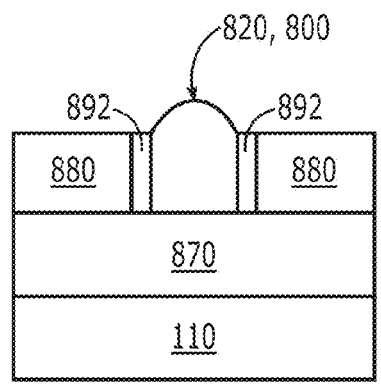
FIG. 9A1
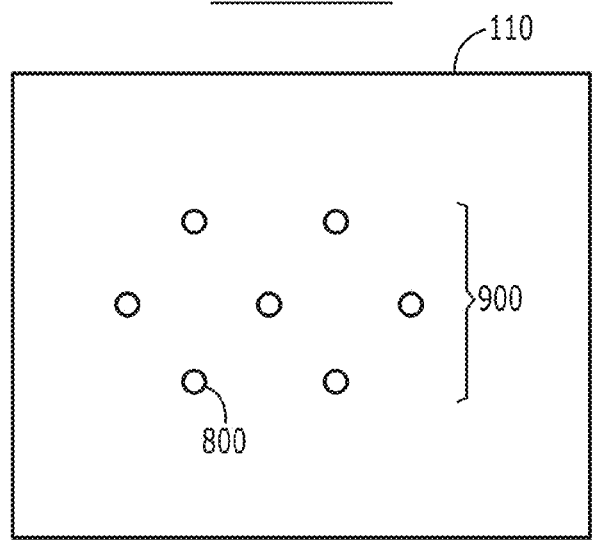
FIG. 9A2
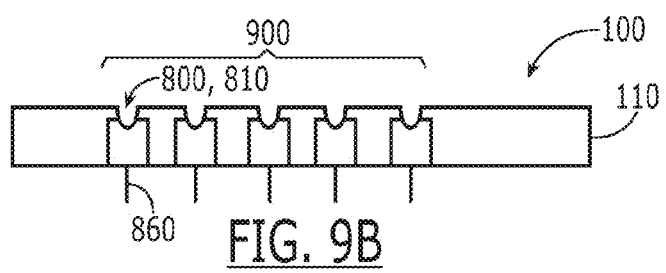
FIG. 9B
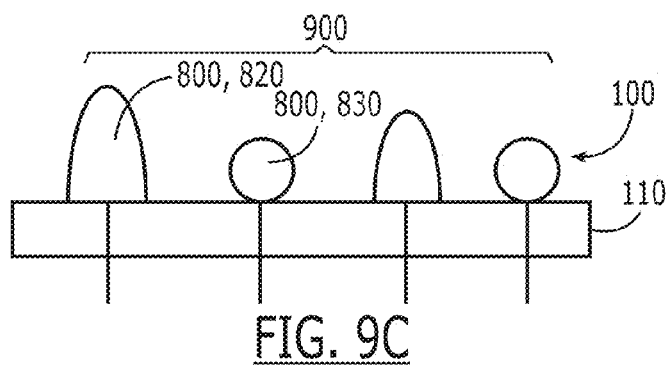
FIG. 9C

NANOSTRUCTURED SUBSTRATES FOR SURFACE ENHANCED RAMAN SPECTROSCOPY (SERS) AND DETECTION OF BIOLOGICAL AND CHEMICAL ANALYTES BY ELECTRICAL DOUBLE LAYER (EDL) CAPACITANCE

CROSS-REFERENCE TO RELATED APPLICATIONS

This application claims priority from U.S. Provisional Application Ser. No. 61/237,034, filed Aug. 26, 2009, and U.S. Provisional Application Ser. No. 61/310,875, filed Mar. 5, 2010, the disclosures of which are hereby incorporated by reference herein in their entirety.

FIELD OF THE INVENTION

The present invention relates to surfaces having nanometer scaled structures. The present invention also relates to surfaces and methods for Surface Enhanced Raman spectroscopy (SERS). The present invention also relates to surfaces and methods for detection of analytes and biological interfacing by electrical double layer (EDL) capacitance.

BACKGROUND OF THE INVENTION

Surface-enhanced Raman Spectroscopy (SERS) is a sensing technique that may be capable of providing relatively fast, specific and label-free detection of spectroscopic fingerprints of molecules adsorbed on metal surfaces. It has been shown that a substantial Raman enhancement may arise from localized spots, or "hot spots," in metallic nanostructures owing to concentrated electromagnetic near-fields associated with strong and localized surface plasmon resonances of some metallic nano-constructs. As such, SERS has been performed on electrochemically roughened metal surfaces, colloids, island films, nanowires, periodic arrays, and self-assembled nanoparticles, and has been used for trace detection of chemical and biological targets. Although these nano features are typically spread over an entire surface, the number of hot spots attainable may be limited and inconsistent. As such, novel substrates and methods for performing SERS may be desirable.

The structure of the electrical double layer (EDL) has been extensively studied over the past century. Based on the classical works by Gouy, Chapman, Stern, Frumkin and Grahame (See Grahame, D. C., *Chem. Rev.*, 41 441 (1947)), a converging picture of the structure of the EDL has emerged. The EDL may be made of a surface-localized part (also referred to as the compact layer) and a thermally mobile and spatially distributed part (also referred to as the diffuse layer). The surface-localized part of the EDL may include localized charges, including electrons, solvent molecules, and/or specifically adsorbed ions, and the thermally mobile and spatially distributed part may include various solvated electroactive and inactive ions. These charged species may cause the EDL structure to act as a capacitor. Aside from some recent efforts made to incorporate nanostructures to a surface to achieve super charge capacitors, there has not been significant progress toward detailed understanding of the EDL structure, or toward utilizing this phenomenon for practical applications.

Recently, the inventor of the present application has investigated the structure and effect of the EDL of a nanometer electrode by a finite-element method. See, Yang, X. and Zhang, G, *Nanotechnology* 18 335201-335209 (2007). This study established that the EDL structure may cause altered current response for nanometer electrodes due to the expansion of the diffuse layer into the diffusion layer, and that the effect of the EDL on the electron transfer and current response of single nanometer electrodes may be significantly influenced by changes in relative-permittivity (or dielectric constant) and compact layer thickness.

In view of the foregoing, novel substrates and methods for practical applications using EDL capacitance may be desirable.

SUMMARY OF THE INVENTION

Provided according to some embodiments of the invention are nanostructured surfaces that include a substrate; and an array of metallic nanopillar islands on the substrate, wherein each metallic nanopillar island may include a metal base layer on the substrate and a plurality of metallic nanopillars on the metal base layer, and wherein portions of the substrate between adjacent metallic nanopillar islands may be free of the metal base layer. In some embodiments, the metallic nanopillar islands may be circular, and in some embodiments, the array of nanopillar islands may have an inter-island distance in a range of about 100 nm to about 1 mm. In some embodiments, each metallic nanopillar island may include a hexagonal array of metallic nanopillars with an inter-pillar distance in a range of about 1 nm to about 500 nm, and the metallic nanopillars may have an aspect ratio in a range of about 1:1 to about 500:1. Furthermore, in some embodiments, the width of the metallic nanopillars may be in a range of about 10 nm to about 500 nm.

In some embodiments of the invention, the metal base layer of the metallic nanopillar islands may include a layer of titanium and/or a layer of gold, and in some embodiments, the plurality of metallic nanopillars include silver and/or gold. In some embodiments, the plurality of nanopillars may include aluminum, silver, gold, copper, titanium and/or tantalum.

According to some embodiments of the invention, the nanostructured surfaces may include other features. For example, in some embodiments, at least one probe molecule may be immobilized on at least one metallic nanopillar island. Additionally, in some embodiments, two or more metallic nanopillar islands may be electrically coupled. Furthermore, in some embodiments, a driver circuit may be in electrical contact with at least one metallic nanopillar island, wherein the driver circuit may be configured to generate an electrical potential sufficient to cause at least a portion of the metallic nanopillars of the at least one metallic nanopillar island to shift position.

In some embodiments of the invention, provided are nanostructured surfaces that include a non-conductive substrate; and at least one nanoelectrode defined within the non-conductive substrate, wherein the at least one nanoelectrode is sized and/or shaped to immobilize an analyte and/or a probe molecule. In some embodiments, the at least one nanoelectrode includes a conductive cavity that is sized and shaped to immobilize a biological analyte. In some embodiments, the conductive cavity is sized and shaped to immobilize a virion. The nanoelectrode may also be a planar conductive surface or may project from the plane of the non-conductive substrate. Nanoelectrodes that project from the plane of the non-conductive substrate include spherical-shaped projection and rod-shaped projections. In some embodiments, the at least one nanoelectrode is present in an array of nanoelectrodes within the non-conductive substrate, and in some embodiments, at least two nanoelectrodes of the array of nanoelectrodes are electrically coupled.

In some embodiments of the invention, the nanostructured surfaces further include at least one analyte and/or probe molecule immobilized by the at least one nanoelectrode, and in some embodiments, the at least one analyte and/or probe molecule include a virion, bacterium or cell.

According to some embodiments of the invention, provided are apparatuses configured to detect an analyte by Surface Enhanced Raman Spectroscopy. In some embodiments, such apparatuses may include (i) a nanostructured surface according to an embodiment of the invention; (ii) a radiation source, the radiation source operable to provide incident radiation to the nanostructured surface; and (iii) a detector, the detector positioned to receive radiation scattered from at least one analyte bound to the nanostructured surface, the scattered radiation being used to detect the at least one analyte. In some embodiments, the incident radiation has a wavelength that excites surface plasmons within a metal in the metal base layer or the metallic nanopillars. In some embodiments, the apparatuses may further include a stage, wherein the nanostructured surface is on the stage; and a controller, wherein the controller is connected to the stage and is configured to translate and/or rotate the stage.

Also provided according to embodiments of the invention are methods of detecting an analyte by Surface Enhanced Raman Spectroscopy that include (i) binding at least one analyte to a nanostructured surface according to an embodiment of the invention; (ii) irradiating the at least one analyte bound to the nanostructured surface; and (iii) detecting radiation scattered by the at least one analyte. In some embodiments, binding of the at least one analyte to the at least one metallic nanopillar island may include electrically charging the metallic nanopillars of the at least one metallic nanopillar island; trapping the at least one analyte within the metallic nanopillars; and discharging the metallic nanopillars. Additionally, in some embodiments, the methods may further include correlating the radiation scattered by the at least one analyte with a chemical structure of the at least one analyte. Furthermore, in some embodiments, the metallic nanopillars may enhance the radiation scattered by the analyte by an enhancement factor in a range of about $10^8$ to about $10^{15}$.

Further provided according to some embodiments of the invention are apparatuses for detecting an analyte or measuring a chemical or biological binding event by electrical double layer capacitance. Such apparatuses may include (i) a nanostructured surface according to an embodiment of the invention; (ii) an electrolyte in contact with at least one metallic nanopillar island/nanoelectrode on the nanostructured surface; (iii) a reference electrode in electrical contact with the electrolyte; and (iv) a meter electrically coupled between the at least one metallic nanopillar island and the reference electrode, wherein the meter is configured to measure capacitances between the at least one metallic nanopillar island/nanoelectrode and the reference electrode. The meter may also be configured to correlate measured capacitances with the presence of an analyte. The apparatuses may further include at least one probe molecule immobilized on at least one metallic nanopillar island/nanoelectrode and the meter may be further configured to correlate measured capacitances with the immobilization of the analyte and/or the binding of at least one analyte to the at least one probe molecule. In some embodiments, the immobilization of the at least one probe molecule may be achieved by electrically charging the metallic nanopillars of at least one metallic nanopillar island; trapping the at least one probe molecule within the metallic nanopillars; and discharging the metallic nanopillars.

Also provided according to some embodiments of the invention are methods of detecting at least one analyte and/or chemical or biological binding of at least one analyte by EDL capacitance that include (i) providing the at least one analyte to an apparatus that includes (a) a nanostructured surface according to an embodiment of the invention; (b) an electrolyte in contact with at least one metallic nanopillar island/nanoelectrode on the nanostructured surface; and (c) a reference electrode in electrical contact with the electrolyte; (ii) measuring capacitances between the at least one metallic nanopillar island/nanoelectrode and the reference electrode; and (iii) correlating the measured capacitances to detect whether the at least one analyte binds to the at least one metallic nanopillar island/nanoelectrode. In some embodiments, at least one probe molecule may be immobilized on at least one metallic nanopillar island/nanoelectrode and the meter may be further configured to correlate measured capacitances to detect the binding of the at least one analyte to the at least one probe molecule. Furthermore, in some embodiments, the at least one probe molecule and the at least one analyte are nucleic acids and the at least one analyte and the at least one probe molecule bind by hybridization. In some embodiments, the at least one analyte and/or the at least one probe molecule is a peptide, protein, virus, nucleotide, cell, bacterium, or synthetic species such as nanoparticle.

BRIEF DESCRIPTION OF THE DRAWINGS

The accompanying drawings, which are included to provide a further understanding of the invention and are incorporated in and constitute a part of this application, illustrate certain embodiment(s) of the invention.

FIG. 1A is an oblique view of an array of metallic nanopillar islands according to some embodiments of the invention.

FIG. 1B is a side view of one of the metallic nanopillar islands in FIG. 1A.

FIGS. 2A1-A5 are SEM images of an array of metallic nanopillar islands, according to some embodiments of the invention, at different magnifications.

FIGS. 2B1-B2 are SEM images of metallic nanopillars, and illustrate bunching of the metallic nanopillars.

FIG. 3 illustrates that a metallic nanopillar island according to some embodiments of the invention may be electrically coupled to a driver circuit 300.

FIGS. 8B(1)-(3), 8C(1)-(3) and 9A1 illustrate methods of forming nanoelectrodes according to some embodiments of the invention.

FIG. 9A2-9C illustrate a plan view (FIG. 9A2) and side views (FIGS. 9B and 9C) of nanostructured substrates according to some embodiments of the invention.

FIG. 10A shows an empty conductive cavity electrode while FIG. 10B shows the same cavity electrode with a virion therein.

FIG. 13A provides the curve for a compact layer thickness (CLT)=0.66 nm and a dielectric constant ($\in$)=6. FIG. 13B provides the curve for a CLT=0.44 nm and $\in$=6.

In FIG. 20A, the dielectrophoretic force attracts an analyte to the nanoelectrode. In FIG. 20B, the charge is reversed and the dielectrophoretic force pushes the analyte from the nanoelectrode.

DETAILED DESCRIPTION OF EMBODIMENTS OF THE INVENTION

Figure 4A:
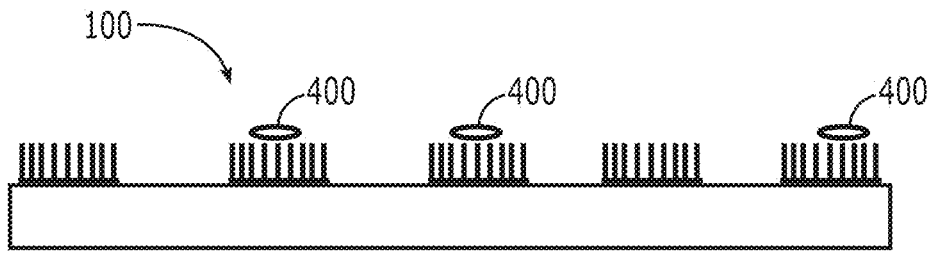
FIGS. 4A-4C illustrate metallic nanopillar islands having analytes (FIGS. 4A and 4B) and/or a probe molecules (FIGS. 4B and 4C) bound thereto.

Embodiments of the present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

Embodiments of the invention are described herein with reference to cross-section illustrations that are schematic illustrations of idealized embodiments (and intermediate structures) of the invention. The dimensions of layers and regions in the drawings may be exaggerated for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this disclosure and the relevant art and will not be interpreted in an idealized or overly formal sense unless expressly so defined herein.

As used herein:

The term "analyte" refers to a chemical or biological entity that can be identified, detected and/or quantified by an analytic process, for example, by a method described herein. For example, for the SERS embodiments described herein, an analyte is a chemical or biological entity that can be detected or quantified by SERS. For the EDL embodiments, an analyte is a chemical or biological entity that can be detected directly or indirectly by EDL capacitance. An analyte may be detected directly when it alters the structure of the EDL of a nanoelectrode. An analyte may be detected indirectly by EDL capacitance when the binding of an analyte to a probe molecule alters the structure of the EDL of a nanoelectrode. The analyte may be a biological analyte or a non-biological analyte, unless otherwise specified.

A "biological analyte" includes microorganism, cells, cell products, or biological molecules, or any other biological analyte known to those of ordinary skill in the art.

A "microorganism" refers to a microscopic living system. Examples of microorganisms include viral particles such as virions, prions or viriods; bacteria; fungi; archea; protists; microscopic algae; plankton; and planarian.

A "cell" includes both prokaryotic and eukaryotic cells, including both natural and recombinant cells. Cell products include constituents of cells such as cell membranes and organelles.

A "biological molecule" refers to a molecule that is produced by a living organism, and also refers to synthetic analogs of such molecules. Examples of biological molecules include carbohydrates such as glucose, disaccharides and polysaccharides; proteins; lipids (including lipid bilayers); and nucleic acids, such as DNA and RNA. Biological molecules may also be small molecules, including monomers and oligomers of other biological molecules, e.g., nucleic acids, nucleotides, fatty acids, etc. The biological molecules may be naturally occurring or synthetic, or may include both naturally occurring and synthetic portions. Thus, the term biological molecule, also includes derivatives such as conjugated nanoparticles of biological molecules.

A "non-biological analyte" refers to an analyte that is not a biological analyte, as defined above. Non-biological analytes may be non-biological molecules. Such molecules may be organic in some embodiments, or inorganic in some embodiments, or a combination of organic and inorganic moieties. A non-biological molecule may be synthetic or naturally occurring. As an example, some synthetic polymer nanoparticles may be non-biological in nature.

A "probe molecule" refers to biological and/or non-biological analytes that may be immobilized on a nanostructured surface according to an embodiment of the invention in order bind or interface with an analyte. Examples include antibody-antigen, protein-ligand, protein-aptamer, paired nucleotides, avidin-biotin, and the like.

I. Nanostructured Surfaces (a) Metallic Nanopillar Islands

Referring to FIG. 1A-1B, provided according to some embodiments of the invention are nanostructured surfaces 100 that include a substrate 110 and an array 120 of metallic nanopillar islands 130 on the substrate 110. Each metallic nanopillar island 130 may include a metal base layer 140 on the substrate 110 and a plurality of metallic nanopillars 150 on the metal base layer 140. In some embodiments, portions of the substrate 110 between adjacent metallic nanopillar islands 130 may be free of the metal base layer 140.

Each metallic nanopillar island 130 may include a metal base layer 140 that includes one or more layers of metal. In some embodiments, the metal base layer 140 may include at least one metal such as silver, gold, titanium, copper, lithium, potassium, sodium, palladium and platinum. In particular embodiments, the metal base layer 140 may include a layer of titanium 170 and/or a layer of gold 180. The plurality of metallic nanopillars 150 may include at least one metal, including aluminum, silver, gold, copper, titanium, tantalum, platinum, lithium, potassium, sodium and/or oxides of these metals.

The metallic nanopillar islands 130 can be in any shape, such as circular, square, triangular, polygon, and the like. Furthermore, the array 120 of metallic nanopillar islands 130 may be in any type of arrangement, including in square or hexagonal patterns. In some embodiments, the array 120 of metallic nanopillar islands 130 has an inter-island distance 190 in a range of about 100 nm to about 1 mm, and in particular embodiments, an inter-island distance 190 in a range of about 500 nm to about 100 μm. As used herein, the inter-island distance 190 is the shortest distance between the outer edges of two neighboring metallic nanopillar islands. In some embodiments, a metallic nanopillar island 130 includes an array (e.g., a hexagonal array) of metallic nanopillars 150 having an inter-pillar distance 195 in a range of about 1, 10 or 20 nm to about 200 or 500 nm, and in particular embodiments, an interpillar distance 195 in a range of about 10 nm to about 200 nm. The interpillar distance 195 is the distance between the centers of two neighboring nanopillars.

The metallic nanopillars 150 may be slender structures of any cross-sectional shape such as circular, square, triangular, polygonal, and the like. In some embodiments of the invention, the metallic nanopillars 150 may have an aspect ratio in a range of about 1:1 or 5:1 to about 50:1, 100:1 or 500:1, and in particular embodiments, an aspect ratio in a range of about 5:1 to about 100:1. In some embodiments, the width 199 of the metallic nanopillars 150 is in a range of about 10 nm to about 500 nm, and in some embodiments, the width 199 of the metallic nanopillars 150 is in a range of about 20 nm to about 200 nm. The width 199 of a cylindrical nanopillar is its diameter. The width 199 of metallic nanopillars 150 having other cross-sectional shapes is the length of a side in the case of polygon-shapes.

Any suitable substrate 110 may be utilized provided that it is non-conductive. In some embodiments, the substrate may be an inert substrate such as glass or silicon.

Referring to FIG. 2A1-2A5, in some embodiments, the metallic nanopillar islands 130 may be electrically coupled for synchronized operation, but in such cases, an insulation gap may still be present to create the desired hot-spots. In some embodiments, the metallic nanopillar islands 130 of the nanostructured surface 100 may be coupled through a metallic bridge 200 that includes a metal base layer 140, and optionally includes metallic nanopillars 150 thereon, and that electrically couples metallic nanopillar islands 130. Any suitable width of metallic bridge 200 may be used, but in some embodiments, the width of the metallic bridge 200 is in a range of about 10 nm to about 10 μm. In some embodiments, the metallic nanopillar islands 130 may be coupled through another mechanism. For example, the metal base layer 140 (not shown) of a particular metallic nanopillar island 130 may be in electrical contact with an electrical lead on or through the underlying substrate 110. In some embodiments, such electrical leads may be electrically coupled with leads connected to other metallic nanopillar islands 130 to allow for synchronized operation.

Referring to FIGS. 2B1 and 2B2, the inventor of the present application (See, Anandan et al., *Int. J. Nanomed.*, 1, 1, 73 (2006)) has demonstrated that when metallic nanopillars 150 have a relatively large aspect ratio (e.g., at least about 30:1), bunching at the top of the metallic nanopillars 150 may occur due to the reduced rigidity of the metallic nanopillars 150 and the presence of a van der Waals attraction between the metallic nanopillars 150. Referring to FIG. 3, in some embodiments, at least one metallic nanopillar island 130 may be electrically coupled to a driver circuit 300. As such, the driver circuit 300 may be in electrical contact with at least one metallic nanopillar island 130, typically through the metal base layer 140, which may be connected to a driver circuit 300 through a metallic bridge 200 (See FIG. 2A2) or an electrical lead on or through the substrate. The driver circuit 300 may be configured to generate an electrical potential sufficient to cause at least a portion of the metallic nanopillars 150 of at least one metallic nanopillar island 130 to shift position. In some embodiments, the distance between the tips of the metallic nanopillars 150 in at least one metallic nanopillar island 130 may be controlled via the driver circuit 300.

Figure 4B:
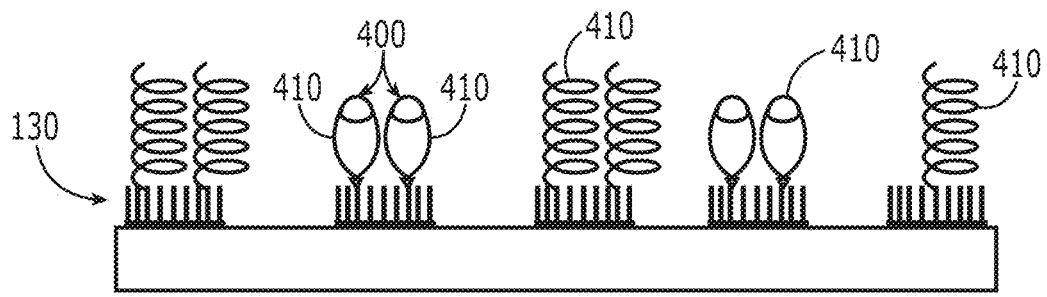
Figure 4C:
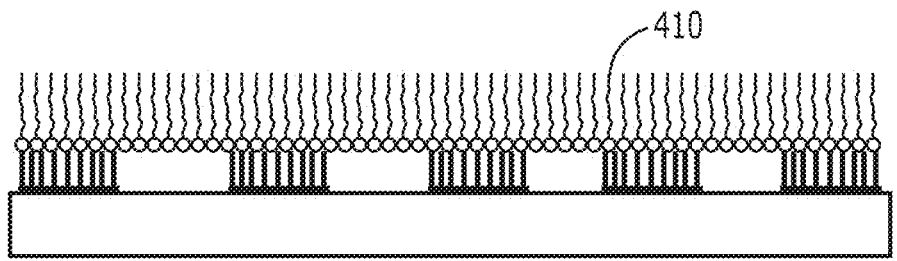
Figure 5A:
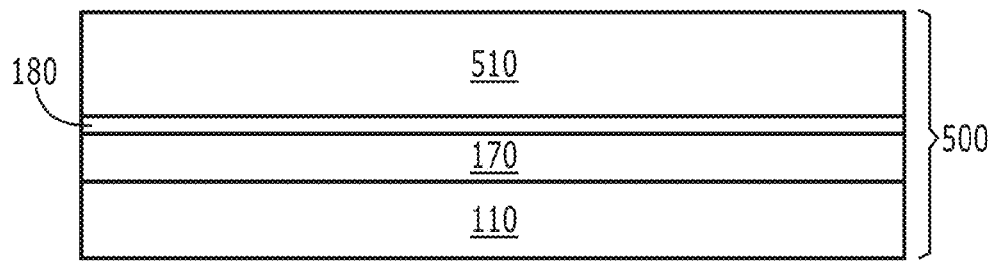
FIGS. 5A-5D illustrate methods of forming metallic nanopillars according to some embodiments of the invention.
Figure 5B:
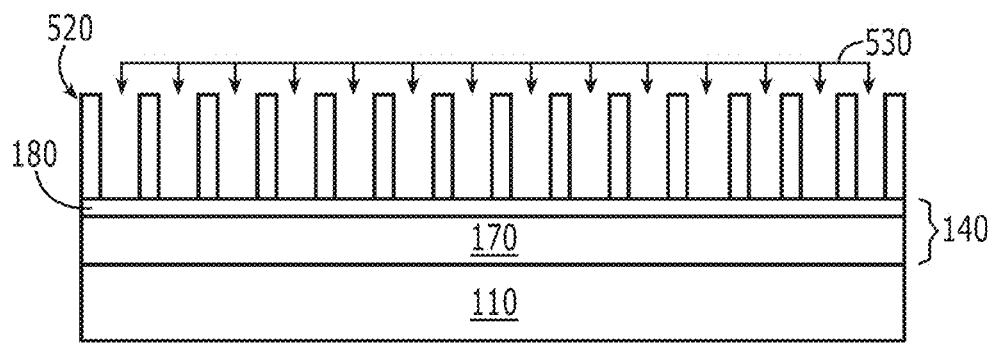
Figure 5C:
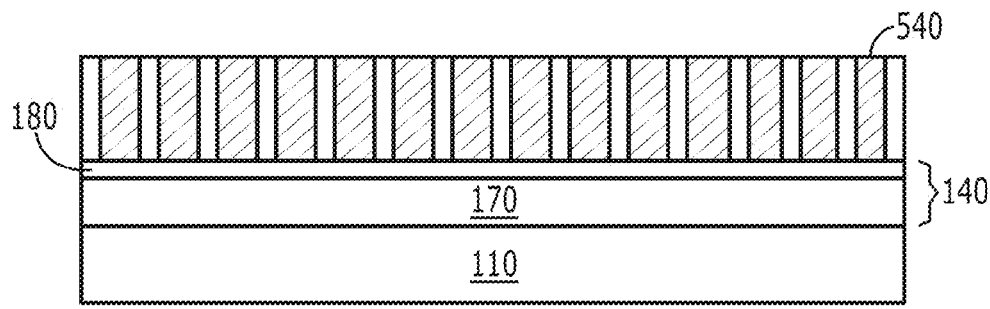
Figure 5D:
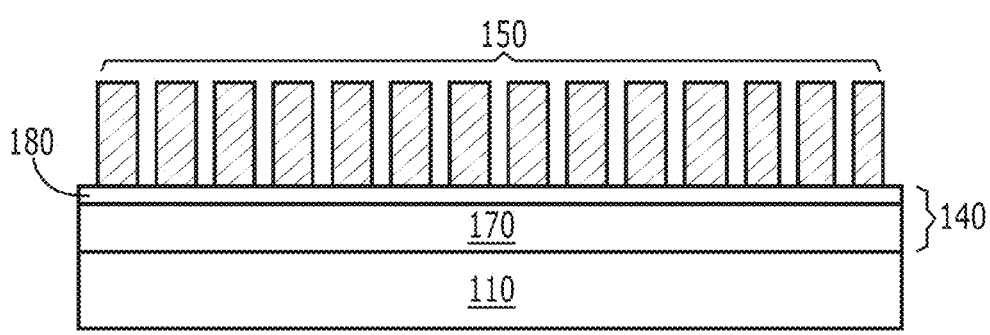

Referring to FIG. 4A, in some embodiments, the nanostructured surface 100 may have at least one analyte 400 bound thereto. The "binding" of an analyte 400 refers to the adsorption and/or chemical binding of an analyte 400 to the nanostructured surface 100 via strong atomic bonds, e.g., ionic, metallic and covalent bonds, and/or weak bonds such as van der Waals, hydrogen, as well as electrostatic attraction and mechanical trapping mechanisms. The "binding" of an analyte 400 also encompasses interfacing. In some embodiments of the invention, at least one analyte 400 is bound to at least one metallic nanopillar island 130. Referring to FIG. 4B-C, in some embodiments, the nanostructured surface 100 includes at least one probe molecule 410 immobilized on at least one metallic nanopillar island 130. The at least one probe molecule 410 may bind to at least one analyte 400, and in some embodiments, may immobilize the at least one analyte 400 on the surface of at least one nanopillar island 130. Immobilization of the at least one probe molecule 410 may be made through any suitable technique. Examples of methods of immobilization of the at least one probe molecule 410 include use of self assembled monolayers (e.g., using alkanethiols), conducting polymers, and the like.

Other binding mechanisms such as electrostatic and mechanical trapping can be used as for immobilizing the at least one analyte 400 or the at least one probe molecule 410. For example, the at least one analyte 400 and/or the at least one probe molecule 410 may be bound to at least one metallic nanopillar island 130 by using a nanostructured surface 100 that is coupled to a driver circuit, as described in FIG. 3. The binding of the at least one analyte 400 and/or the at least one probe molecule 410 may be achieved by electrically charging the metallic nanopillars 150 of at least one metallic nanopillar island 130; trapping the at least one analyte 400 and/or the at least one probe molecule 410 within the metallic nanopillars 150; and discharging the metallic nanopillars 150.

The at least one analyte 400 and/or the at least one probe molecule 410 may be applied to a nanostructured surface 100 by any suitable method. However, in some embodiments, the at least one analyte 400 and/or the at least one probe molecule 410 may be applied to a nanostructured surface 100 by applying a solution, e.g., a droplet, including the at least one analyte 400 and/or the at least one probe molecule 410 to the nanostructured surface 100. In some embodiments, a voltage (e.g., an AC voltage) may be applied to generate a dielectrophoretic force to attract the at least one analyte 400 and/or the at least one probe molecule 410 to the metallic nanopillars 150. Once there, the AC signal may be turned off but the at least one analyte 400 and/or the at least one probe molecule 410 may be immobilized on the metallic nanopillars due to van der Waals forces. Any suitable concentration may be used for applying the at least one analyte 400 and/or the at least one probe molecule 410 to the nanostructured surface 100. For example, the concentrations may vary from single molecules to 2M, 3M, 4M, or higher, solutions.

The nanostructured surfaces described herein may be formed by any suitable method. In some embodiments of the invention, the nanostructured surface may be produced by (i) forming an array of metallic nanopillars on a metal base layer on a substrate (See FIGS. 5A-D); (ii) masking the array of metallic nanopillars (See FIGS. 6A-C); (iii) etching the exposed portions of the array of metallic nanopillars and the metal base layer underlying the exposed portion of the metallic nanopillars (See FIG. 7A); and (iv) removing the mask on the array of metallic nanopillars to form an array of metallic nanopillar islands on the substrate (See FIG. 7B).

Referring to FIGS. 5A-D, the array of metallic nanopillars 150 may be formed on the substrate 110 by any suitable method. However, in some embodiments, the array of metallic nanopillars 150 may be formed by a method described in U.S. application Ser. No. 12/232,152, filed on Sep. 11, 2008, U.S. application Ser. No. 12/382,860, filed on Mar. 25, 2009, U.S. application Ser. No. 12/382,861, filed on Mar. 25, 2009 and/or U.S. application Ser. No. 12/825,897, filed Jun. 29, 2010, the contents of each of which are incorporated herein by reference in their entirety. In these methods, an array of metallic nanopillars 150 may be formed by methods that include forming a base 500 that includes aluminum 510 (See FIG. 5A); anodizing the base 500 that includes aluminum 510 to form aluminum oxide 520 having a hexagonal array of nanopores 530 defined therein (See FIG. 5B); depositing a conductive material 540 into the nanopores of the hexagonal array of nanopores 530 (See FIG. 5C); and removing the aluminum oxide 520 to provide the array of metallic nanopillars 150 (See FIG. 5D). In some embodiments, the base 500 that includes aluminum 510 may include a non-conductive substrate 110, a titanium layer 170 on the substrate 110, a gold layer 180 on the titanium layer 170, and the aluminum 510 on the titanium layer 170.

Figure 6A:
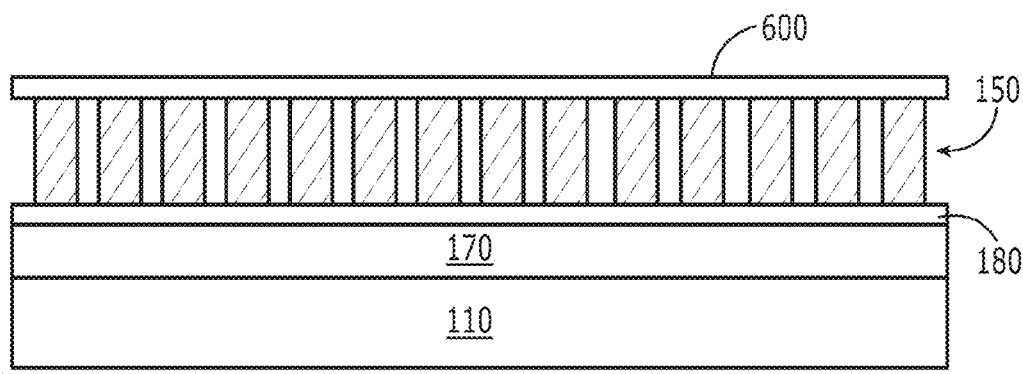
FIGS. 6A-6C illustrate methods of forming a photoresist pattern according to some embodiments of the invention.
Figure 6B:
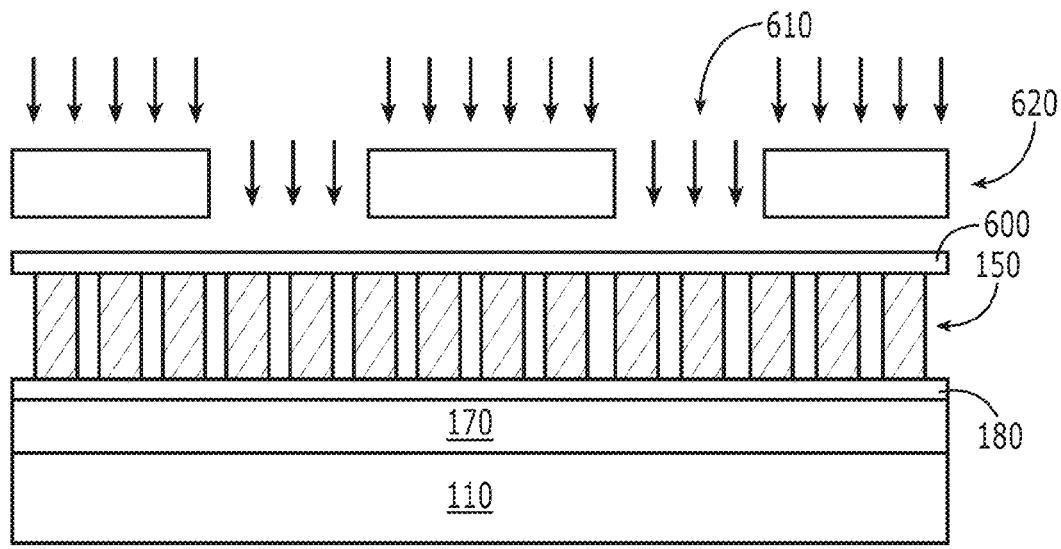
Figure 6C:
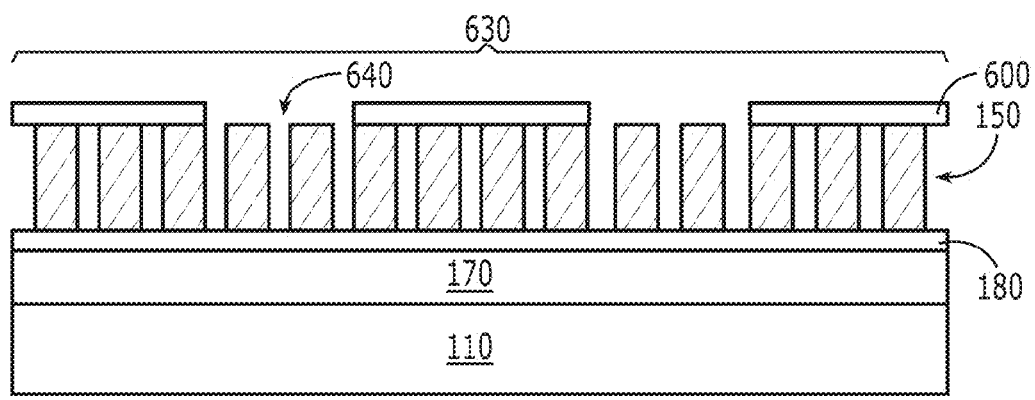

Referring to FIGS. 6A-C, masking of the array of metallic nanopillars 150 may be achieved by any suitable method. However, in some embodiments, the masking is achieved by coating the array of metallic nanopillars 150 with a photoresist 600 (See FIG. 6A); selectively irradiating 610 portions of the photoresist 600 by use of a photomask 620 (See FIG. 6B); and developing the photoresist 600 to create a photoresist pattern 630 (See FIG. 6C). Any suitable photoresist 600 may be utilized, including positive and negative photoresists. As such, developing the photoresist 600 may selectively remove the irradiated portions (positive resist) or the masked portions (negative resist) to provide exposed portions 640 of the array of metallic nanopillars 150. FIGS. 6A-C illustrate an embodiment that uses a positive photoresist. In some embodiments, the photoresist 600 may be a Shipley 1818 positive photoresist.

Figure 7A:
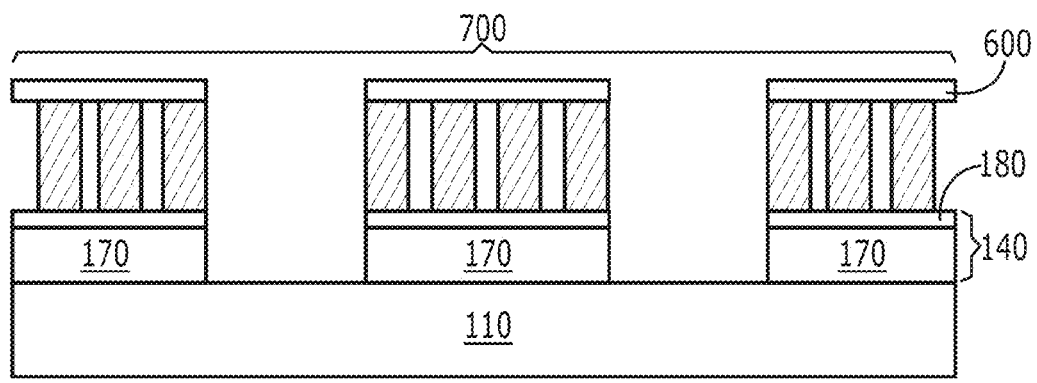
FIG. 7A-7B illustrate etching of the exposed portions of a metallic nanopillar array to form metallic nanopillar islands according to some embodiments of the invention.
Figure 7B:
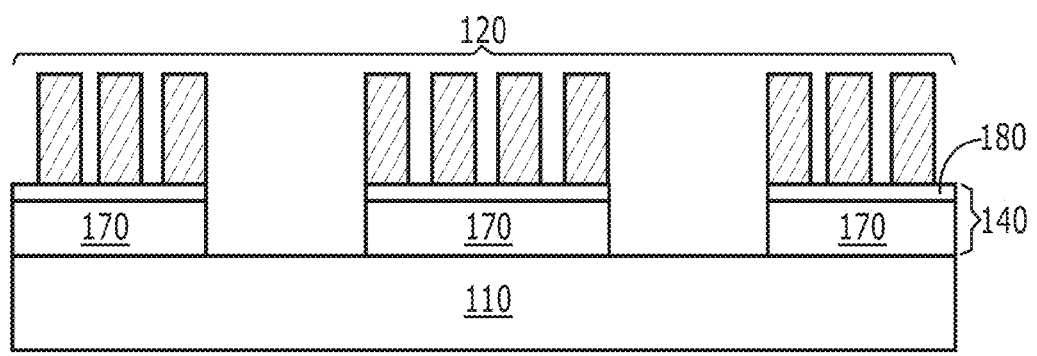

Etching of the exposed portions 640 of the array of metallic nanopillars 150 and the underlying metal base layer 140 may be achieved by any suitable method. In some embodiments, the exposed portions 640 of the array of metallic nanopillars 150 and/or the underlying metal base layer 140 may be etched using an acid, such as phosphoric acid. In some embodiments, the exposed portions 640 of the array of metallic nanopillars 150 and/or the underlying metal base layer 140, and particularly a gold layer 180 of the metal base layer 140, may be etched using a solution of potassium iodide, iodine and/or water. Further, in some embodiments, the exposed portions 640 of the array of metallic nanopillars 150 and/or the underlying metal base layer 140, particularly a titanium layer 170 of the metal base layer 140, may be etched in a solution containing water, hydrofluoric acid and/or peroxide. Referring to FIG. 7A, the etching of the exposed portions 640 of the array of metallic nanopillars 150 and the underlying metal base layer 140 may result in an array of photoresist-covered metallic nanopillars islands 700. The photoresist 600 may then be removed from the photoresist-covered metallic nanopillars islands 700 to provide the array 120 of metallic nanopillar islands 130 (See FIG. 7B). The photoresist 600 may be removed by any suitable method, and in some embodiments, is removed with a chemical photoresist stripper.

(b) Other Nanoelectrodes

Figure 8A:
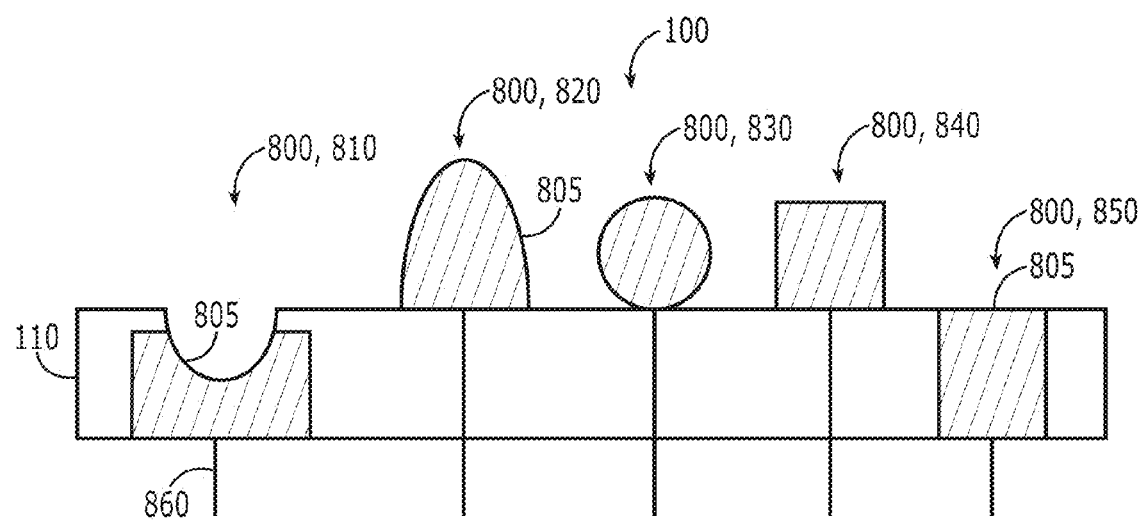
FIG. 8A illustrates side views of nanoelectrodes according to some embodiments of the invention.

Referring to FIG. 8A, provided according to some embodiments of the present invention is a nanostructured surface 100 that includes a non-conductive substrate 110; and at least one nanoelectrode 800 defined within the non-conductive substrate 110, wherein the at least nanoelectrode 800 is sized and/or shaped to bind an analyte 400 and/or probe molecule 410 (not shown). As shown in FIG. 8A, the nanoelectrode 800 may be any suitable shape. For example, the nanoelectrode 800 may be shaped as a conductive cavity 810, including a cavity having a spherical, ellipsoidal, cylindrical, cuboid or polyhedron shape; or the nanoelectrode 800 may be a projection such as rod-shaped projection 820 (e.g., a cylinder or polyhedron), a spherical-shaped projection 830, or a cuboid-shaped projection 840. In some embodiments, the nanoelectrode 800 may also be a flat or planar electrode 850 of any shape in the x-y plane, such as circle, triangle, square, rectangle or polygon.

The at least one nanoelectrode 800 includes a conductive surface 805. In some embodiments, the entire surface of the at least one nanoelectrode 800 may be a conductive surface 805. However, in some embodiments, only a portion of the surface 805 of the at least one nanoelectrode 800 includes a conductive surface 805. Additionally, in some embodiments, the conductive surface 805 of the at least one nanoelectrode 800 may also be coupled 860 to at least one other nanoelectrode 800 and/or a reference electrode or meter. In some embodiments, the nanoelectrode 800 may be coupled via a conductive lead that partially or completely traverses the non-conductive substrate 110, as shown in FIG. 8A. However, in some embodiments, the nanoelectrode 800 may be coupled through conductive leads on the surface of the non-conductive substrate 110. Any suitable conductive material may be used for the conductive surface 805 of the at least one nanoelectrode 800. However, in some embodiments, the conductive surface 805 may include platinum, gold, titanium, copper, carbon, indium tin oxide and/or a conductive polymer. Any suitable non-conductive substrate 110 may be utilized provided that it is non-conductive. In some embodiments, the substrate may be an inert substrate such as glass or silicon.

The nanoelectrode 800 may be formed by any suitable method. However, in some embodiments of the invention, the nanoelectrode 800 may be formed by one of the methods described below. Referring to FIG. 8B1, a gold film 870 may be deposited on a non-conductive substrate 110, such as a silicon wafer, for example by E-beam evaporation. The gold film 870 may be patterned into individual islands, and in some embodiments, such islands may be networked with wiring leads. A layer of silicon dioxide 880 may then be deposited, e.g., by using Atomic Layer Deposition, and may also be coated with a photoresist layer 890. Other materials may be used in lieu of silicon dioxide, including, for example, AlN, $Al_2O_3$, GaAs, GaN, $In_2O_3$, InN, and the like.

In some embodiments, a nanoelectrode 800 may be formed by creating a hole, e.g., in a range of about 10 nm to about 1 µm, in the photoresist layer 890, for example, by E-beam lithography, and then transferring the hole pattern to the silicon dioxide layer 880 (See FIG. 8B2). This results in a flat plane electrode 850 within a cuboid cavity. The flat plane electrode 850 may be resized to a desired dimension by any suitable method. However, referring to FIG. 8B3, in some embodiments, the flat plane electrode 850 may be resized by depositing a layer of aluminum oxide 892, for example, by atomic layer deposition, and anisotropically etching the aluminum oxide 892 to remove excess aluminum oxide 892 to form the resized flat plane electrode 894 set within a cuboid cavity, as shown in FIG. 8C1. In some embodiments, a flat plane electrode 850, as shown in FIG. 8B2, or a resized flat plane electrode 894, as shown in FIG. 8C1, may be further etched to form a conductive cavity 810, as shown in FIG. 8C2. Any suitable etching process may be used, such as a wet etching or a dry Ar-plasma. In some embodiments, a metal deposition process, e.g., a gold deposition process, may be applied to a flat plane electrode 850, as shown in FIG. 8B2, or a resized flat plane electrode 894, as shown in FIG. 8C1, to form flat plane electrode 850 on the surface, as shown in FIG. 8C3. In some embodiments, the silicon dioxide 880 and aluminum oxide 892, if present, of the flat plane electrode 850 may be partially etched to form a gold projection structure 820 as the nanoelectrode 800. The aforementioned provides only some methods of forming nanoelectrodes 800 according to embodiments of the invention. Other suitable known techniques for forming metallic structures may be used to form nanoelectrodes 800.

Referring to FIGS. 9A2-9C, in some embodiments of the invention, the at least one nanoelectrode 800 is present as an array of nanoelectrodes 900 within the non-conductive substrate 110. Each nanoelectrode 800 may be independent, or in some embodiments, two or more of the nanoelectrodes 800 of the array of nanoelectrodes 900 may be electrically coupled, as described above. In some embodiments, the array of nanoelectrodes 900 may include only one type of nanoelectrode 800. For example, FIG. 9B shows an array of nanoelectrodes 900 that only includes conductive cavities 810. In some embodiments, two or more different types of nanoelectrodes 800 may be present in the array of nanoelectrodes 900. For example, FIG. 9C shows an array of nanoelectrodes 900 that includes both rod-shaped projections 820 and spherical-shaped projections 830.

An analyte 400 and/or probe molecule 410 (not shown) is immobilized by the nanoelectrode 800 when at least a portion of the analyte 400 or probe molecule 410 interfaces with the nanoelectrode 800 such that they are bound by some chemical, electrical and/or mechanical force to the nanoelectrode 800. Further, in some embodiments, a probe molecule 410 may be immobilized by the nanoelectrode and the analyte 400 may be immobilized by the probe molecule 410.

Figure 10A:
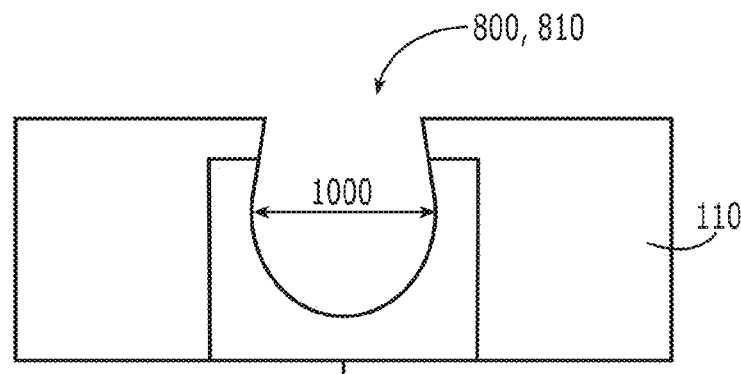
FIG. 10A and FIG. 10B illustrate an expanded side view of a conductive cavity electrode according to some embodiments of the invention.
Figure 10B:
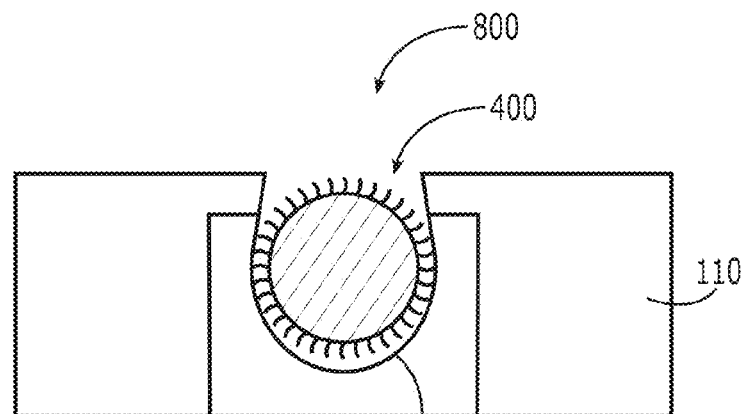
Figure 10C:
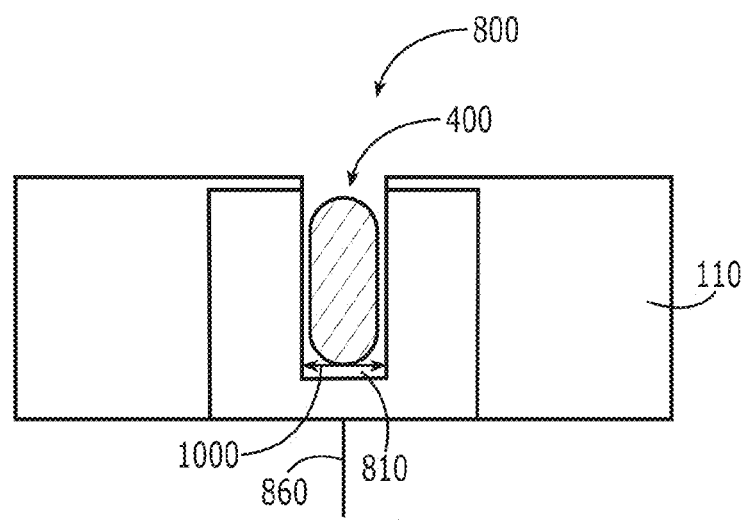
FIG. 10C illustrates a conductive cavity electrode having a different size and shape than those shown in FIGS. 10A and 10B.

The shape of the nanoelectrode 800 may facilitate mechanical binding which may serve as a selective mechanism to target a particular analyte 400 or probe molecule 410. For example, referring to FIGS. 10A-C, in some embodiments, analyte 400 may be immobilized in a nanoelectrode 800 that is a conductive cavity 810 when at least a portion of the analyte 400 is sized and/or shaped to become immobilized by the conductive cavity 810. In particular embodiments, the analyte 400 may be a virion that is sized and/or shaped to become immobilized by the conductive cavity 810. As such, in some embodiments, the conductive cavity 810 may be sized and shaped to fit an entire virion, and in some embodiments, the conductive cavity 810 may be sized and shaped to fit a portion of a particular virion. In some embodiments, the at least one conductive cavity 810 has a width 1000 in a range of about 10 nm to about 500 nm. The term "width" in this context refers to the largest distance across the conductive cavity. In FIGS. 10A-B, the conductive cavity 810 is spherical, thus being suited to immobilize an analyte 400 that is spherical and of the appropriate size. As another example, in FIG. 10C, the conductive cavity 810 is cylindrical, thus being suited to immobilize an analyte 400 that is cylindrical and of the appropriate size. Thus, the size and shape of the conductive cavity 810 may be tailored to a particular type of analyte 400 and/or probe molecule 410.

II. SERS Applications

Figure 11:
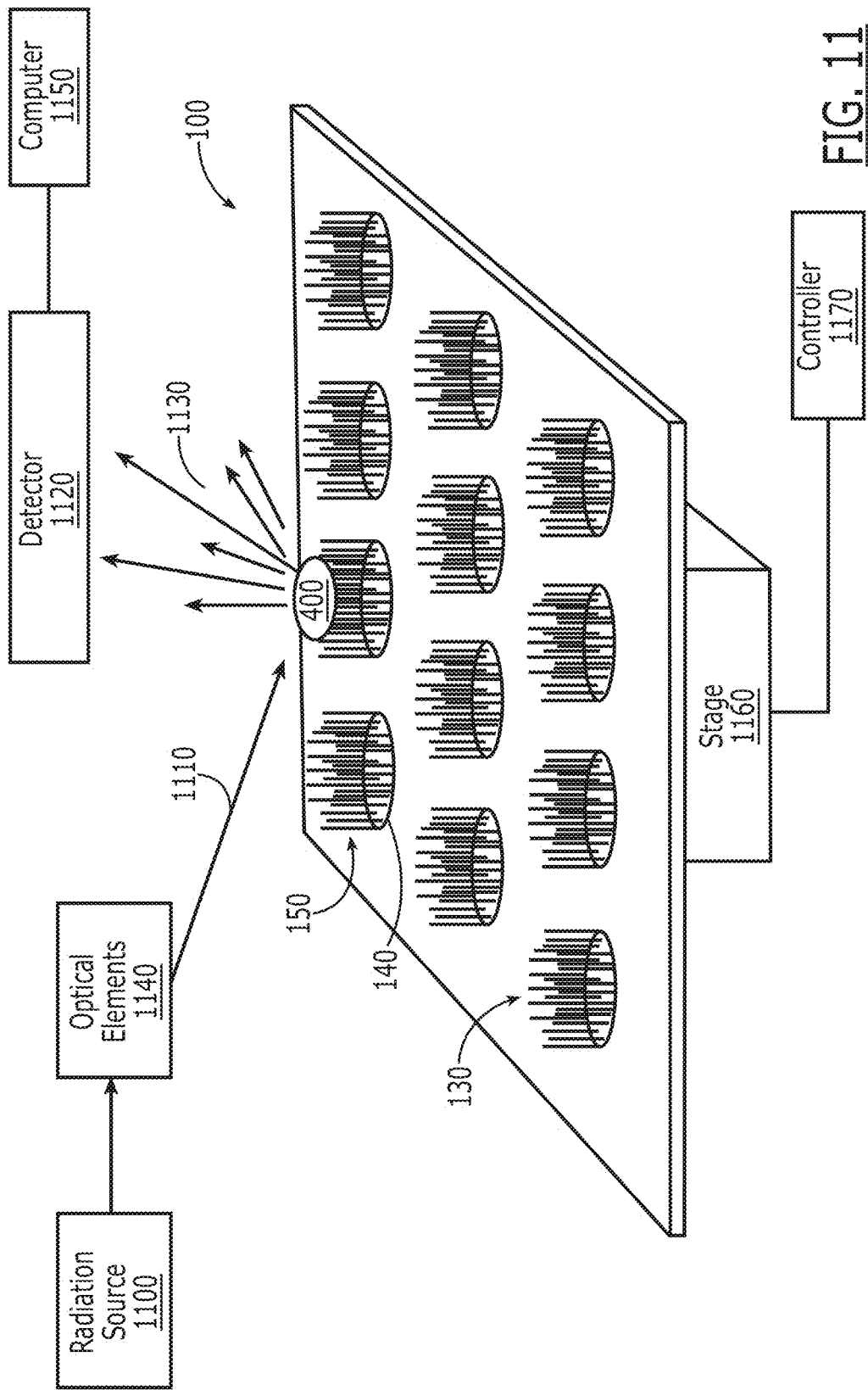
FIG. 11 illustrates a SERS apparatus according to some embodiments of the invention.

Any suitable Surface Enhanced Raman Spectroscopy (SERS) apparatus may be used in combination with the nanostructured surfaces described herein. However, provided herein are SERS apparatuses configured to detect an analyte on a nanostructured surface according to some embodiments of the invention. Referring to FIG. 11, such apparatuses may include (i) a nanostructured surface 100 according to some embodiments of the invention; (ii) a radiation source 1100, the radiation source 1100 operable to provide incident radiation 1110 to the nanostructured surface 100; and (iii) a detector 1120, the detector 1120 positioned to receive scattered radiation 1130 from at least one analyte 400 bound to the nanostructured surface 100, the scattered radiation 1130 being used to detect the at least one analyte 400.

Any suitable radiation source 1100 may be used, but in some embodiments, the radiation source is a laser beam source. As shown in FIG. 11, in some embodiments, the SERS apparatus may include additional optical elements 1140 to process the radiation, such as optical elements 1140 that focus and/or deflect (e.g., lenses and/or mirrors) the radiation from the radiation source 1100 to provide the incident radiation 1110. In some embodiments, the incident radiation 1110 (the radiation irradiating the nanostructured surface 100) may have a wavelength that excites surface plasmons within the metal base layer 140 and/or the metallic nanopillars 150 of at least one metallic nanopillar island 130 on the nanostructured surface 100. At least one analyte 400 bound to the nanostructured surface 100 may scatter the incident radiation 1110, and at least a portion of the scattered radiation 1130 may be Raman scattering, which has a frequency that is different, and typically lower, than the incident radiation 1110. At least a portion of the scattered radiation 1130 may be collected by a detector 1120. Furthermore, analytical equipment, such as a computer 1150, may be programmed to process the information from the detector 1120 and generate a Raman spectrum. In some embodiments, the same computer 1150 or a different computer 1150 may process the Raman spectrum to identify the at least one analyte 400.

In some embodiments of the invention, the nanostructured surface 100 may be on a stage 1160. This stage 1160 may be connected to a controller 1170, which may move the stage 1160 in the linear and/or rotational translations as desired, so that different portions of the nanostructured substrate 100 (e.g., different metallic nanopillar islands) may be irradiated by incident radiation 1110 and analyzed as desired. In some embodiments, the operation of the stage 1160 and the controller 1170 may be synchronized with other portions of the SERS apparatus to automate radiation and detection of at least one analyte 400 on at least one metallic nanopillar island 130, thereby automating detection of at least one analyte 400 on at least one predefined hotspot (defined by the metallic nanopillar islands). In some embodiments, a driver circuit 300, as described with reference to FIG. 3, may be in electrical contact with at least one metallic nanopillar island 130 of the nanostructured surface 100. Furthermore, in some embodiments, at least one probe molecule 410, as described with reference to FIG. 4, may be immobilized on at least one metallic nanopillar island 130. The at least one probe molecule 410 may aid in the binding at least one analyte 400 to the metallic nanopillar island 130. Additionally, the skilled artisan will appreciate that different individual apparatuses may work in concert to form apparatuses according to embodiments of the invention.

According to some embodiments of the invention, provided are methods of detecting an analyte 400 by SERS that include (i) binding at least one analyte 400 to a nanostructured surface 100 according to an embodiment of the invention, (ii) irradiating the at least one analyte 400 bound to the nanostructured surface 100; and (iii) detecting radiation scattered 1130 by the at least one analyte 400. In some embodiments, the at least one analyte 400 is bound to at least one metallic nanopillar island 130, and in some embodiments, the at least one analyte 400 may be bound to two or more metallic nanopillar islands 130. Additionally, in some embodiments, methods further include correlating the scattered radiation 1130 from the at least one analyte 400 with a chemical structure of the at least one analyte 400, e.g., by using computer 1150.

In some embodiments, the binding of the at least one analyte 400 to the at least one metallic nanopillar island 130 includes electrically charging the metallic nanopillars 150 of the at least one metallic nanopillar island 130; trapping the at least one analyte 400 within the metallic nanopillars 150; and discharging the metallic nanopillars 150. The charging of the metallic nanopillars 150 may be achieved, for example, when at least one metallic nanopillar island 130 is electrically coupled to a driver circuit 300, as shown in FIG. 3. Both positive and negative electrical charges may be applied to the metallic nanopillar islands 130, and the type of charge applied may depend on the charge status of the at least one analyte 400. In some embodiments, at least one probe molecule 410, as shown in FIG. 4, may be immobilized on a metallic nanopillar island 130, and the at least one analyte 400 may bind to the at least one probe molecule 410.

In some embodiments, the metallic nanopillars 150 and/or the underlying metal base layer 140 may enhance the radiation scattered by the at least one analyte 400 by an enhancement factor in a range of about $10^8$ to about $10^{15}$. As used herein, the enhancement factor is the field intensity ratio at a hotspot of an enhanced surface to that of an unenhanced surface.

The nanostructured surfaces, SERS apparatuses and SERS methods described herein may provide advantageous features for analyte detection. For example, the nanostructured surfaces described herein may provide hot spots at predetermined locations, which may allow for relatively fast and automated optical reading schemes. Furthermore, when a driver circuit is electrically coupled to at least one metallic nanopillar island on the nanostructured surface, a desired amount of electrical charge can be applied to the metallic nanopillars to shift (e.g., open a bunched portion of metallic nanopillars) ends of the metallic nanopillars to allow for mechanical trapping of analytes into hot spots. This trapping of analytes into hot spots by mechanical bunching of the nanopillars may avoid the need for the use of anchoring or probe molecule, thus bringing the analyte closer to the electromagnetic near-fields for enhanced optical interrogation.

II. Biological and Chemical Sensing Applications

Figure 12A:
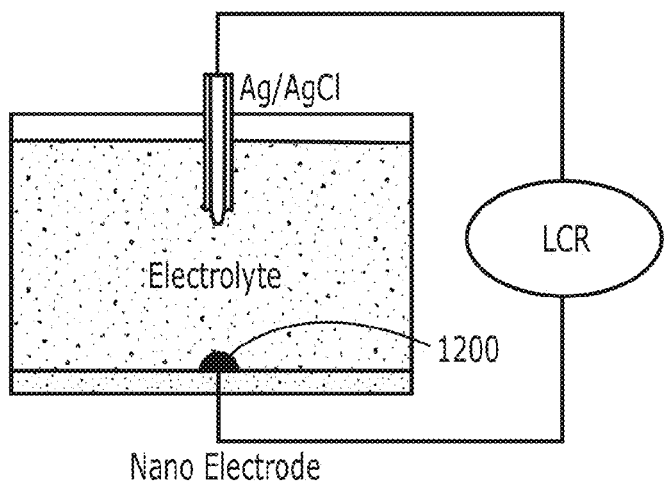
FIG. 12A illlustrates the electrochemical model used in a simulation for calculating properties related to the EDL capacitance of a nanoelectrode.

Recently, a computational approach to simulate the electrochemical processes of nanometer electrodes based on a finite element analysis was developed by the inventor of the present application. See Yang X. and Zhang G., *Nanotechnology*, 18, 335201, 1-9, (2007), which is incorporated herein by reference in its entirety. A brief description of this computational approach and the results of this study follow. For the electrochemical environment surrounding a nanometer spherical electrode 1200 shown in FIG. 12A, a cyclic electrical overpotential (E) is applied to the nanometer electrode 1200 (radius=1 nm) to polarize the electrode 1200 and the surrounding electrical double layer (EDL) structure as well as the electrolyte 1210. The resulting electrical field ($\phi$) sur rounding the electrode is determined. The EDL capacitance is calculated using the following formula:

$$C_{EDL} = \varepsilon\varepsilon_0\left(\frac{\partial^2 \phi}{\partial r \cdot \partial E}\right).$$

See, Bard and Faulkner, *Electrochemical Methods*, John Wiley & Sons, Inc. 2001.

Figure 12B:
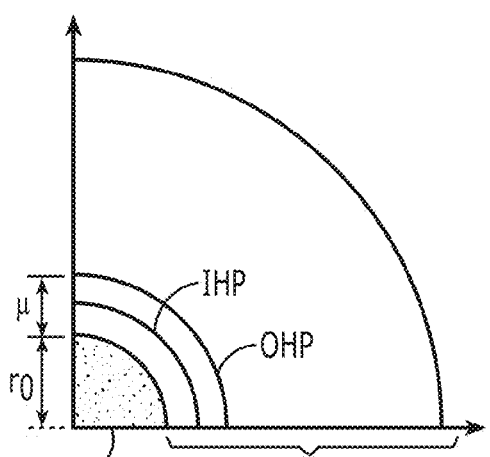
FIG. 12B illustrates a 2D axisymmetric geometric model depicting a spherical nanometer electrode surrounded by an EDL structure in an electrolytic solution. The shaded quarter-circle represents the electrode, IHP=inner Helmholtz plane and OHP=outer Helmholtz plane.
Figure 12C:
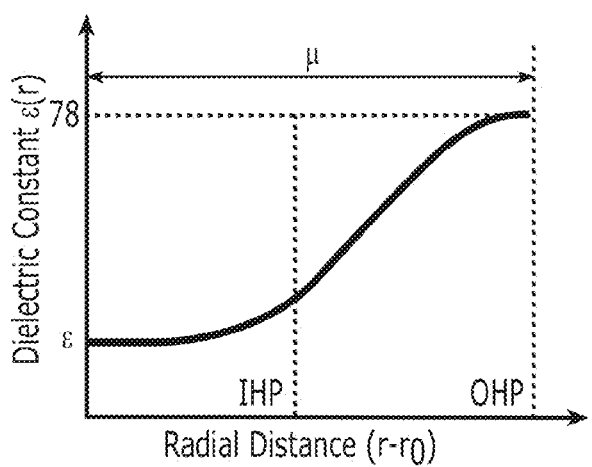
FIG. 12C is a diagram illustrating the dielectric constant of the compact layer of the EDL as a function of the radial distance.

As schematically shown in FIG. 12B, a two-dimensional (2D) quarter-circle geometric model in a cylindrical coordinate system (u, v) is considered to represent a three-dimensional (3D) spherical electrode 1200 by taking advantage of the axisymmetery (about the u-axis) and the in-plane symmetry (about the v-axis). In this model, an electrode 1200 of radius $r_0$ is placed at the origin of the coordinate system. The space surrounding the electrode 1200 is divided into two domains: the first represents the electronic compact layer of the EDL of the electrolyte 1210 located within $r_0 \leq r < r_0 + u$ (note $r = \sqrt{(u^2 + v^2)}$), and the second represents the electrolyte 1210 located between $r = r_0 + \mu$ and $r = 1000 r_0$. Inside the compact layer, there is an inner Helmholtz plane (IHP) and an outer Helmholtz plane (OHP). In the calculations, it is assumed that there is no specific ionic adsorption at the surface of the electrode 1200; thus, the region inside the IHP is mainly filled with solvent molecules without any ions. Furthermore, it is also assumed that the OHP is the plane of closest approach for all the ions (active and inactive), and is the position of electron transfer, which means that electron transfer between the electrode 1200 and the electrolyte 1210 occurs here. Referring to FIG. 12C, it is assumed that the dielectric constant c varies smoothly and continuously inside the compact layer of the electrolyte 1210.

Figure 13A:
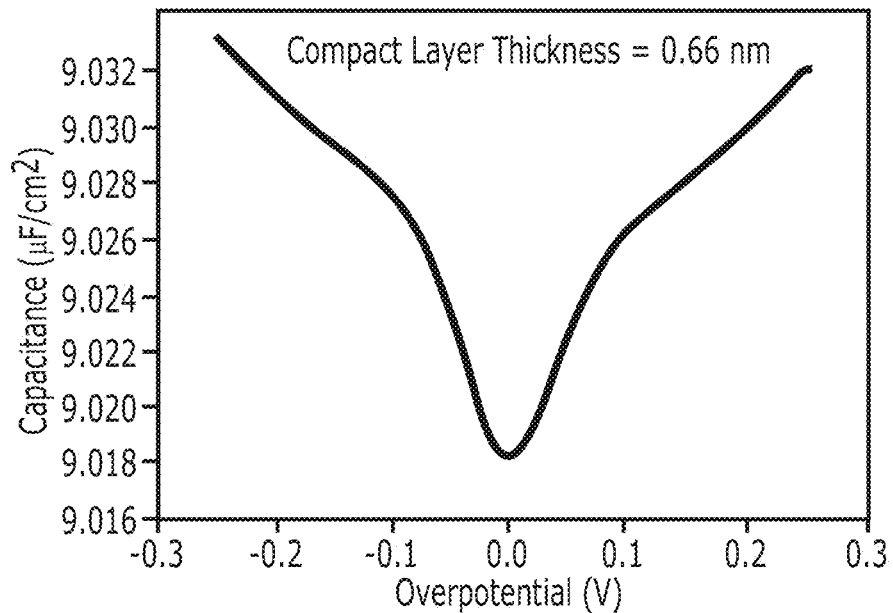
FIG. 13A and FIG. 13B provide typical curves for variations of EDL capacitance with electrical overpotential for two cases.
Figure 13B:
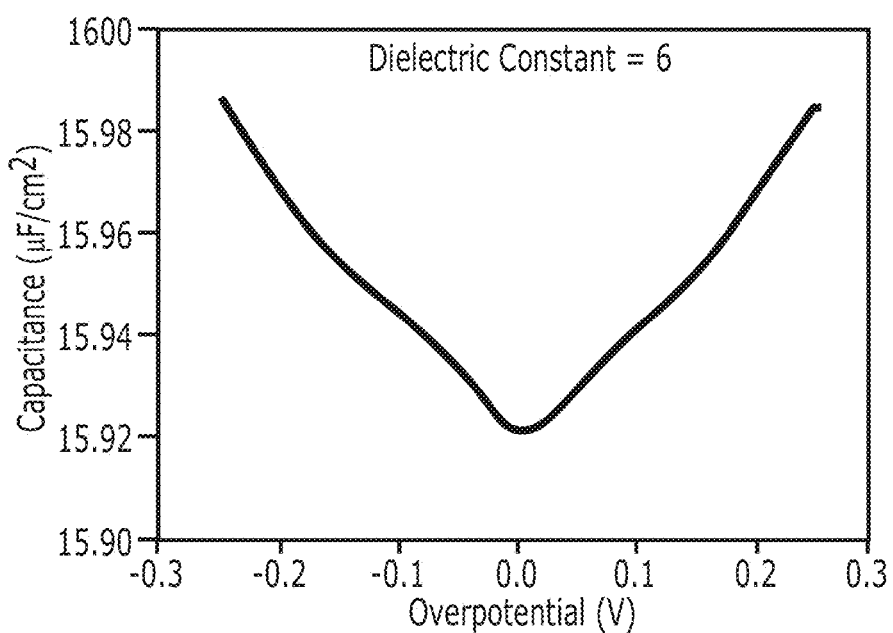
Figure 14:
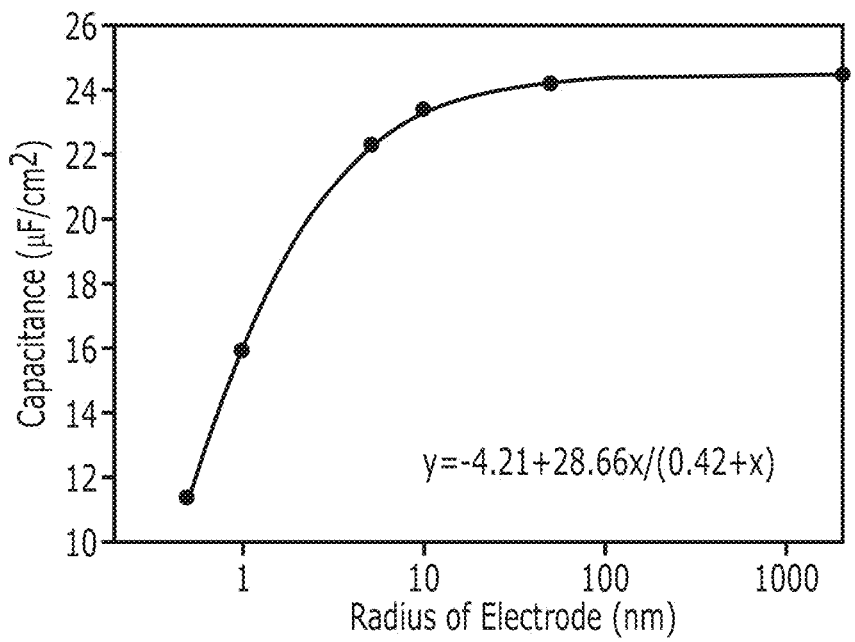
FIG. 14 is a graph illustrating variations of EDL capacitance with the radius of the electrode.
Figure 15:
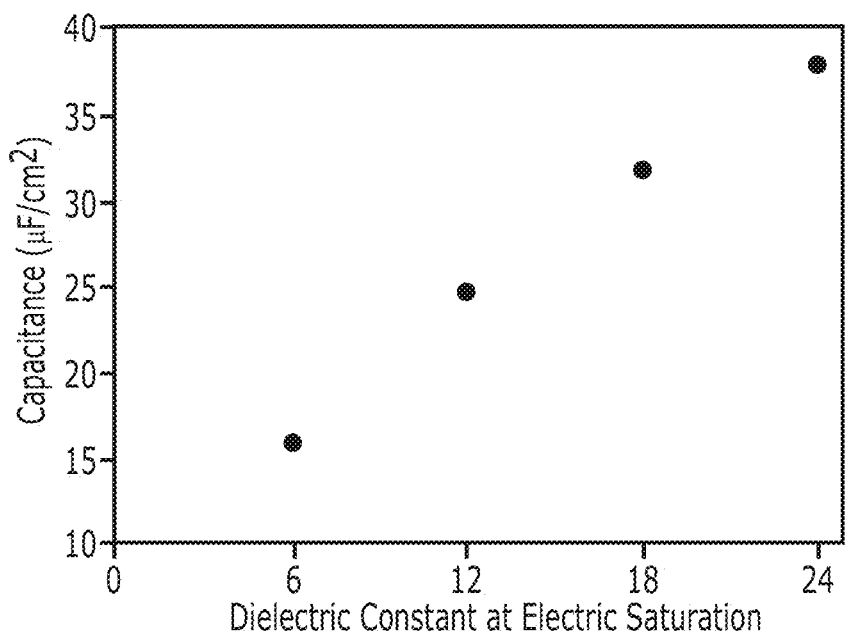
FIG. 15 is a graph illustrating variations of EDL capacitance with the dielectric constant at electrical saturation.
Figure 16:
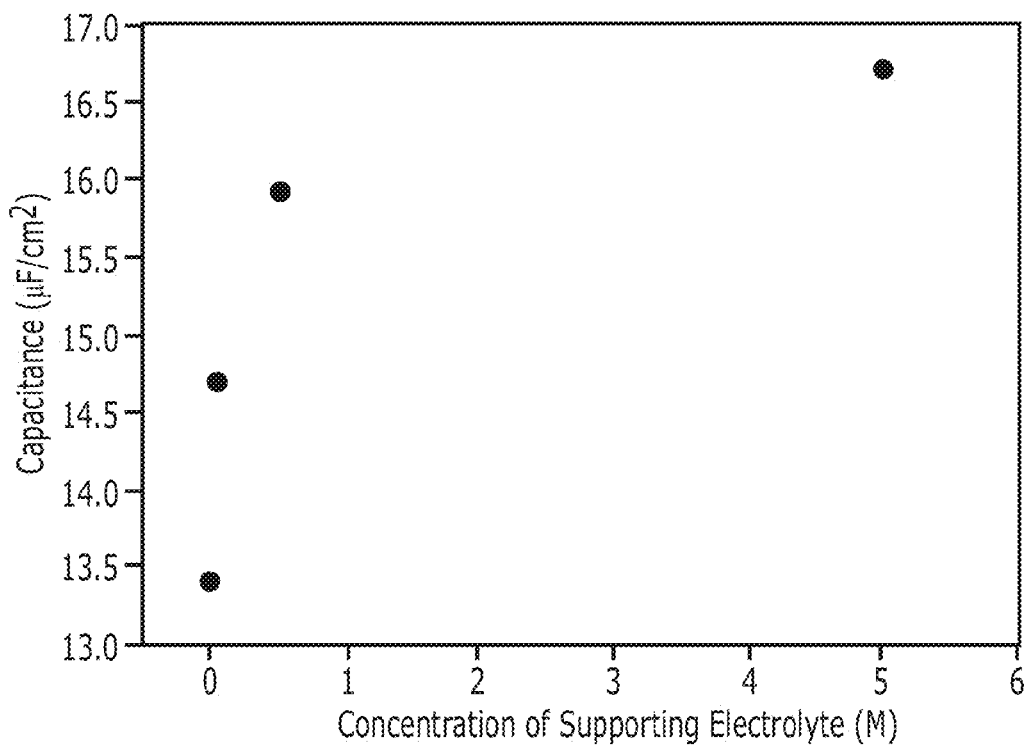
FIG. 16 is a graph illustrating variations of EDL capacitance with the concentration of the supporting electrolyte.
Figure 17:
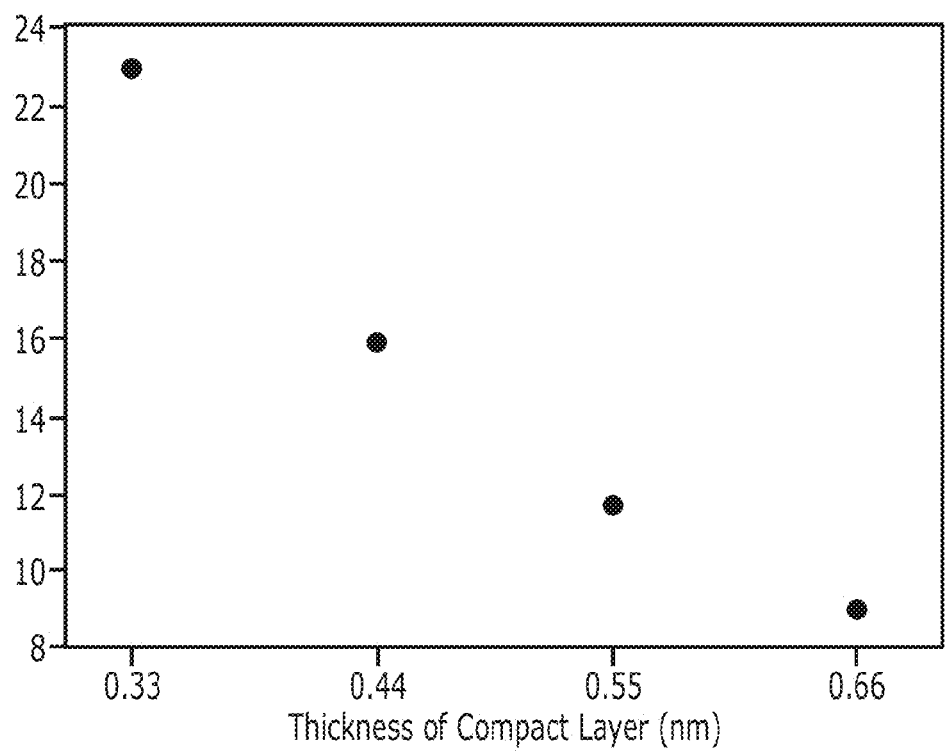
FIG. 17 is a graph illustrating variations of EDL capacitance with the thickness of the compact layer.

Selected results obtained from these computational analyses are provided in FIGS. 13-17. FIG. 13 shows two examples in which the EDL capacitance as a function of overpotential is plotted, when the compact layer thickness (CLT) is 0.66 nm and the dielectric constant ($\in$) is 6 (FIG. 13A) and when the CLT is 0.44 nm and $\in$ is 6 (FIG. 13B). FIG. 14 is a graph depicting the variation of EDL capacitance with the radius of the electrode. FIG. 15 is a graph depicting the variation of EDL capacitance with the dielectric constant at electrical saturation. FIG. 16 is a graph depicting the variation of EDL capacitance with the concentration of the supporting electrolyte. FIG. 17 is a graph depicting the variation of EDL capacitance with the thickness of the compact layer.

This data shows that the capacitance of the EDL structure surrounding a nanometer electrode 1200 (See FIGS. 12A-12B) may be heavily influenced by changes in dielectric constant in the compact layer and diffuse layer, as well as compact layer thickness and the bulk electrolyte concentration. Thus, since the compact layer and the nearby diffuse layer have dimensions on the scale of several angstroms to a few nanometers, a nanoelectrode 1200 may be used to discriminate changes in the charge and dielectric state in an electrolyte 1210 spanning from the nanoelectrode 1200 surface to a few nanometers out.

As shown in FIG. 17, an increase in the thickness ($\mu$) of the compact layer surrounding a 1-nm spherical electrode from 0.33 to 0.66 nm may cause a significant drop in capacitance from about 23 to 9 $\mu F/cm^2$. Further, an increase in dielectric constant ($\in$) at the electrode surface from 6 to 24 may cause a significant increase in capacitance from about 16 to 38 $\mu F/cm^2$ (See FIG. 15). As a reference, $\mu$ usually varies from 0.3 to 0.7 nm depending on the size of the ionic species in the electrolyte; $\in$ changes from 6 for a highly saturated ionic electrolyte to 78 for water. Thus, the charge (both electronic and ionic) distribution and the dielectric profile in the compact layer and in the nearby diffuse layer may affect the electrical property of the EDL structure in a very sensitive way.

In view of the foregoing, apparatuses and methods that utilize the sensitivity of the capacitance between a nanoelectrode and a reference electrode to the charge distribution and the dielectric properties of the EDL are described herein.

(a) Analyte Detection by EDL Capacitance—Metallic Nanopillars

Figure 18:
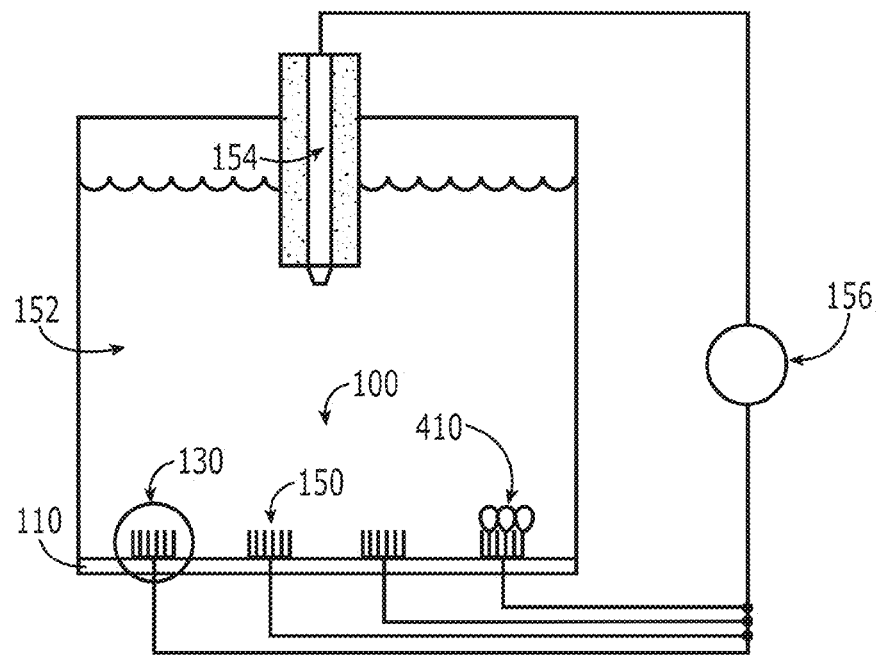
FIG. 18 illustrates an apparatus for the detection of biological or chemical interfacing according to some embodiments of the invention.

According to some embodiments of the invention, provided are apparatuses for detecting an analyte or measuring a biological binding event by electrical double layer capacitance. Referring to FIG. 18, in some embodiments, such apparatuses may include (i) a nanostructured surface 100 according to an embodiment of the invention; (ii) an electrolyte 152 in contact with at least one metallic nanopillar island 130 on the nanostructured surface 100; (iii) a reference electrode 154 in electrical contact with the electrolyte 152; and (iv) a meter 156 electrically coupled 860 between the at least one metallic nanopillar island 130 and the reference electrode 154. In some embodiments, the meter 156 may be configured to measure capacitances between the at least one metallic nanopillar island 130 and the reference electrode 154. In some embodiments, the meter 156 may measure capacitances between one metallic nanopillar island 130 and the reference electrode 154, and in some embodiments, the meter 156 may measure capacitances between two or more of the metallic nanopillar islands 130 and the reference electrode 154. In some embodiments, the meter 156 is configured to correlate the capacitances to detect the presence of at least one analyte 400 (not shown).

As used herein, the reference electrode 154 is one or more electrodes that provide a reference (e.g. a particular reference voltage) for measurements recorded from at least one metallic nanopillar island 130. Examples of reference electrodes include a standard hydrogen electrode (SHE), an Ag/AgCl reference electrode, a saturated calomel electrode (SCE), and/or a Cu/Cu(II) reference electrode.

As used herein, the meter 156 may include one or more devices such as a voltmeter, multi-meter or other capacitance and/or impedance measurement equipment, as well as other electronic equipment used to obtain, process or analyze data obtained from the capacitance measurements. The meter 156, for example, may be configured to apply an AC electrical signal between a metallic nanopillar island 130 and the reference electrode 154, and to use the applied AC electrical signal to determine a capacitance between the metallic nanopillar island 130 and the reference electrode 154.

The electrolyte 152 may include any suitable electrolyte or combination of electrolytes. Examples of electrolytes include aqueous solutions of KCl, NaCl and phosphate buffered saline (PBS). In some embodiments, the molarity of the electrolyte is 0.001 M to 2 M, and in some embodiments, the pH is in a range of 7 and 7.4.

In some embodiments, at least one probe molecule 410 may be immobilized on the nanostructured surface. In some embodiments, the at least one probe molecule 410 may be bound to at least one metallic nanopillar island 130. Further, in some embodiments, at least one analyte 400 and/or at least one probe molecule 410 may be mechanically trapped by the metallic nanopillars 150 of the metallic nanopillar island 130. In some embodiments, a driver circuit 300, as shown in FIG. 3, may be electrically coupled to at least one metallic nanopillar island 130, and its ability to charge the metallic nanopillars 150 of the at least one metallic nanopillar island 130 may facilitate the mechanical and/or electrostatic trapping of the at least one probe molecule 410. When at least one analyte 400 interfaces or binds to the at least one probe molecule 410, the charged nature of the at least one probe molecule 410, the at least one analyte 400, and the EDL of the surrounding electrolyte may be altered. Thus, the capacitance measured between the at least one metallic nanopillar island 130 and the reference electrode 154 may also be altered. Therefore, the interfacing or binding of the at least one analyte 400 to the at least one probe molecule 410 may be detected by analyzing the change in capacitance. In some embodiments, the meter 156 may be further configured to correlate measured capacitances with binding of at least one analyte 400 to the at least one probe molecule 410.

According to some embodiments of the invention, methods of detecting at least one analyte 400 and/or a biological or chemical binding event by EDL capacitance may include (i) providing at least one analyte 400 to an apparatus that includes (a) a nanostructured surface according to an embodiment of the invention; (b) an electrolyte 152 in contact with at least one metallic nanopillar island 130 on the nanostructured surface 100; and (c) a reference electrode 154 in electrical contact with the electrolyte 152; (ii) measuring capacitances between the at least one metallic nanopillar island 130 and the reference electrode 154; and (iii) correlating the measured capacitances to detect whether the at least one analyte 400 is bound to the at least one metallic nanopillar island 130.

In some embodiments, the methods may be performed when at least one probe molecule 410 is immobilized on at least one metallic nanopillar island 130. Further, in some embodiments, the measured capacitances may be correlated to detect whether the at least one analyte 400 binds or interfaces with the at least one probe molecule 410. In some embodiments, the at least one probe molecule 410 and the at least one analyte 400 are nucleic acids and the at least one analyte 400 and the at least one probe molecule 410 bind by hybridization. In some embodiments, the at least one analyte 400 and/or the at least one probe molecule 410 is a protein, virus, nucleotide, lipid bilayer, cell membrane, cell, bacterium, or conjugated nanoparticle. In some embodiments, the at least one probe molecule 410 may include a biological species that spans two or more metallic nanopillar islands 130, and the measurement of capacitance at predetermined metallic nanopillar islands 130 in the presence of an analyte 400 may provide information regarding localized binding events in the biological species or their chemo-structural information.

According to some embodiments of the invention, the nanopillars 150 may also be used as an electrode for redox purposes. This unique feature may become desirable when a analyte is prone to electrochemical oxidation. When oxidation (i.e., electron transfer) of the analyte occurs, a lower capacitance value is expected. This information can be used to identify a particular analyte.

The apparatuses and method for detecting biological binding described herein may be used to detect the presence of an analyte, to detect a biological binding event, and to characterize molecular structures. In some embodiments, the apparatuses described herein may provide numerous parallel nano or micro-sized EDL capacitors that may expand the detection range and increase the detection sensitivity of an analyte. Another advantage of the apparatuses described herein is that a charged electrolytic species may enter the space in between nanopillars from beneath the probe molecules, in addition to from the side and above, which may lead to enhanced detection sensitivity.

(b) Analyte Detection by EDL Capacitance with Other Nanoelectrodes

Figure 19:
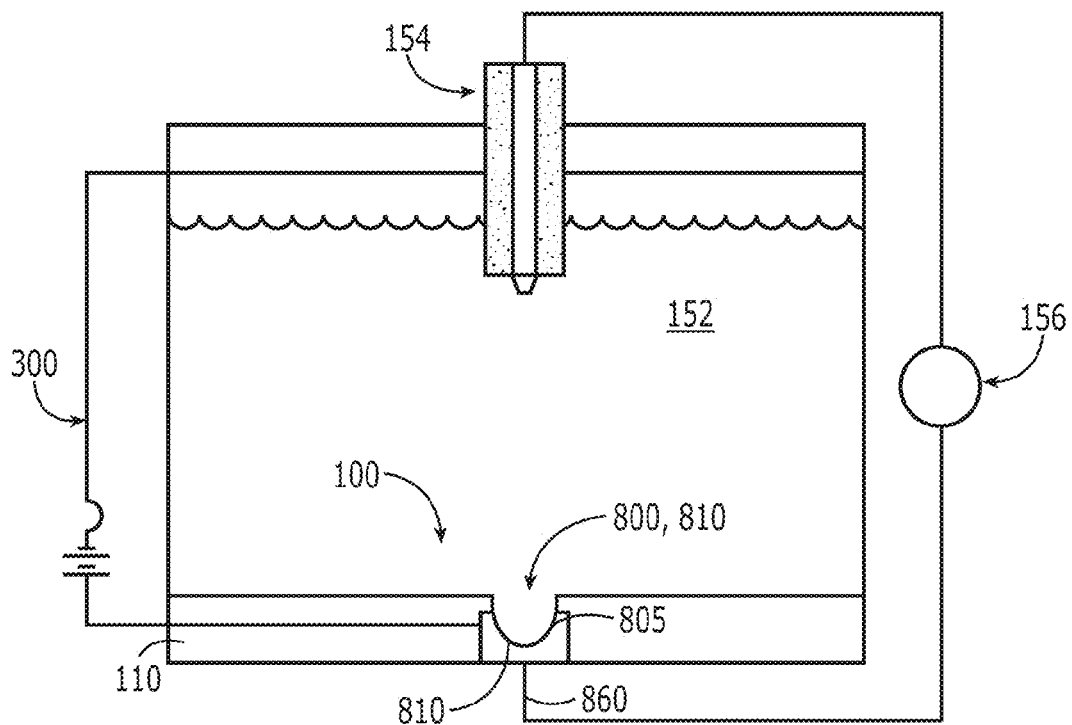
FIG. 19 illustrates an apparatus for the detection of an analyte according to some embodiments of the invention.

According to some embodiments of the invention, provided are other apparatuses for detecting an analyte by EDL capacitance. Referring to FIG. 19, in some embodiments, such apparatuses may include (i) a nanostructured surface 100 that includes a non-conductive substrate 110 and at least one nanoelectrode 800 defined within the non-conductive substrate 110, wherein the at least one nanoelectrode 800 is sized and/or shaped to immobilize an analyte 400 and/or probe molecule 410 (not shown); (ii) an electrolyte 152 in contact with at least one nanoelectrode 800 on the nanostructured surface 100; (iii) a reference electrode 154 in electrical contact with the electrolyte 152; and (iv) a meter 156 electrically coupled 820 between the at least one nanoelectrode 800 and the reference electrode 154. In such, case, the conductive surface 805 of the at least one nanoelectrode 800 may act as an electrode for EDL capacitance measurements. In some embodiments, the meter may be further configured to correlate measured capacitances with the immobilization of the analyte 400 and/or the probe molecule 410 by the at least one nanoelectrode 800. The meter may also be configured to correlate measured capacitances with the binding of an analyte 400 to a probe molecule 410 that is bound to at least one nanoelectrode 800.

In some embodiments, the meter 156 may be configured to measure capacitances between the at least one nanoelectrode 800 and the reference electrode 154. In some embodiments, the meter 156 may measure capacitances between one nanoelectrode 800 and the reference electrode 154, and in some embodiments, the meter 156 may measure capacitances between two or more of nanoelectrodes 800 and the reference electrode 154. In FIG. 19, the nanoelectrode 800 shown is a conductive cavity 810, but any of the nanoelectrodes 800 described herein may be used in apparatuses according to embodiments of the invention.

As used herein, the reference electrode 154 is one or more electrodes that provide a reference (e.g. a particular reference voltage) for measurements recorded from the at least one conductive cavity 800. Examples of reference electrodes include a standard hydrogen electrode (SHE), an Ag/AgCl reference electrode, a saturated calomel electrode (SCE), and/or a Cu/Cu(II) reference electrode.

As used herein, the meter 156 may include one or more devices such as a voltmeter, multi-meter or other capacitance measurement equipment, as well as other electronic equipment used to obtain, process or analyze data obtained from the capacitance measurements. The meter 156, for example, may be configured to apply an AC electrical signal between a conductive cavity 800 and the reference electrode 154, and to use the applied AC electrical signal to determine a capacitance between the conductive cavity 800 and the reference electrode 154.

The electrolyte 152 may include any suitable electrolyte or combination of electrolytes. Examples of electrolytes include aqueous solutions of KCl, NaCl and phosphate buffered saline (PBS). In some embodiments, the molarity of the electrolyte is 0.001 M to 2 M, and in some embodiments, the pH is in a range of 7 and 7.4.

Figure 20A:
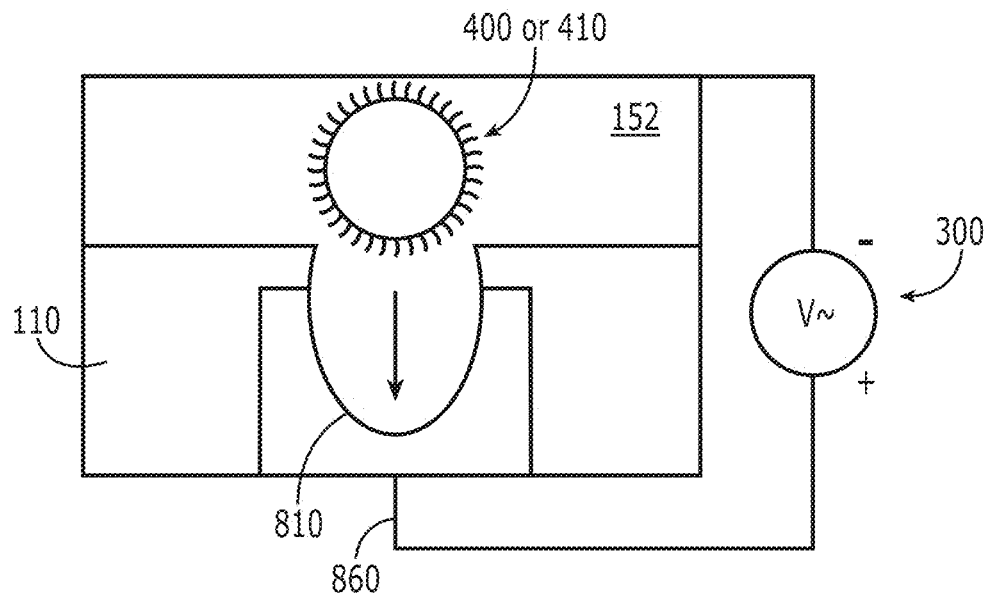
FIGS. 20A-B illustrates an expanded side view of the nanoelectrode shown in FIGS. 10A and 10B in combination with a driver circuit.
Figure 20B:
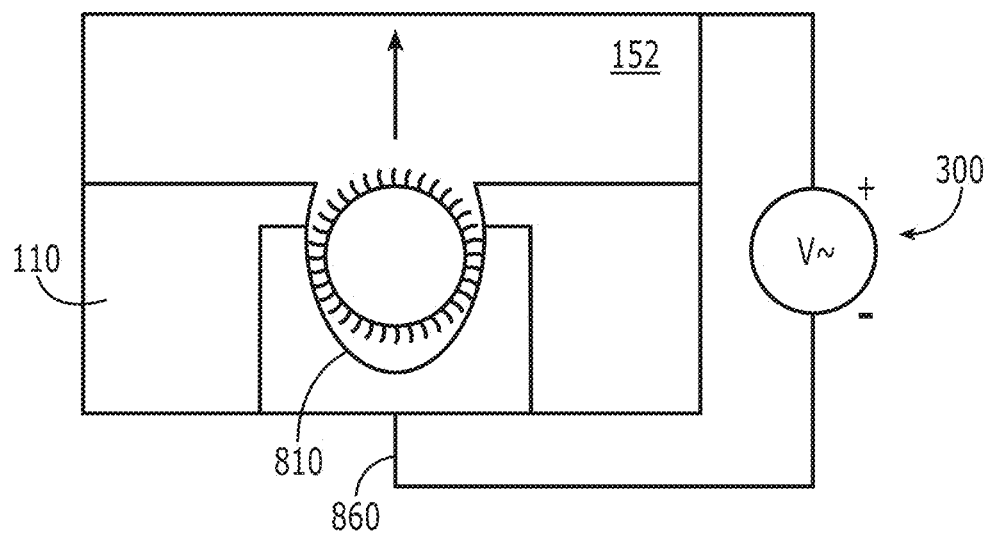

Referring to FIG. 20, in some embodiments, at least one analyte 400 and/or probe molecule 410 may be immobilized by the at least one nanoelectrode 800 on the nanostructured surface 100. In some embodiments, a driver circuit 300, as shown in FIGS. 20A and 20B, may be electrically coupled to at least one nanoelectrode 800, and its ability to charge the conductive surface 805 of the at least one nanoelectrode 800 may facilitate immobilization via mechanical and/or electrostatic trapping of the at least one analyte 400 and/or probe molecule 410 by the nanoelectrode 800. While the driver circuit 300 in FIGS. 20A and 20B is an AC circuit, one of skill in the art would understand that other configurations, such as a DC circuit, may also be used. When the at least one analyte 400 and/or probe molecule 410 is immobilized by the nanoelectrode 800, the charged nature of the analyte 400 and the EDL of the surrounding electrolyte may be altered. Thus, the capacitance measured between the at least one nanoelectrode 800 and the reference electrode 154 may also be altered. Therefore, the presence of the at least one analyte 400 and/or probe molecule 410 may be detected by analyzing the change in capacitance. In FIG. 20, the nanoelectrode 800 is a conductive cavity 810, but other suitable nanoelectrodes, such as the other nanoelectrodes described herein, may be used.

As discussed above, in some embodiments, the meter 156 may be further configured to correlate measured capacitances with immobilization of the at least one analyte 400 and/or probe molecule 410 by the nanoelectrode 800, or the immobilization of the analyte 400 by a probe molecule 410 that is immobilized by the nanoelectrode 800. In such a case, each nanoelectrode 800 may immobilize only one analyte 400 and/or probe molecule 410, as shown in FIG. 20B, or may immobilize more than one analyte 400 and/or probe molecule 410. As shown in FIG. 20B, the at least one analyte 400 and/or probe molecule 410 may be released from the nanoelectrode 800 by reversing the polarity of the dielectrophoretic force of the driver circuit 300, thus repelling the at least one analyte 400 and/or probe molecule 410 from the nanoelectrode 800. FIGS. 20A and 20B illustrate the example of a conductive cavity 810 but any of the nanoelectrodes described herein may be used according to embodiments of the invention.

According to some embodiments of the invention, methods of detecting at least one analyte 400 and/or a biological or chemical binding event by EDL capacitance include (i) providing the at least one analyte 400 and/or probe molecule 410 to an apparatus that includes (a) a nanostructured surface 100 that includes a non-conductive substrate 110 and at least one conductive cavity 800 defined within the non-conductive substrate 110, wherein each conductive cavity 800 is sized and/or shaped to immobilize the analyte 400 and/or a probe molecule 410; (b) an electrolyte 152 in contact with at least one conductive cavity 800 on the nanostructured surface 100; and (c) a reference electrode 154 in electrical contact with the electrolyte 152; (ii) measuring capacitances between the at least one conductive cavity 800 and the reference electrode 154; and (iii) correlating the measured capacitances to detect whether the analyte 400 is immobilized by the nanoelectrode 800 and/or bound to a probe molecule 410 that is immobilized by the nanoelectrode 800.

The apparatuses and methods described herein may be used to detect the presence of an analyte, such as a biological analyte. In some embodiments, the apparatuses described herein may provide numerous parallel nano or micro-sized EDL capacitors that may expand the detection range and increase the detection sensitivity of an viral detection.

Further, according to some embodiments of the invention, the nanoelectrode 800 may also be used as an electrode for redox purposes. This unique feature may become desirable when a analyte is prone to electrochemical oxidation. When oxidation (i.e., electron transfer) of the analyte occurs, a lower capacitance value is expected. This information can be used to identify a particular analyte.

The present invention will now be described in more detail with reference to the following example. However, this example is given for the purpose of illustration and is not to be construed as limiting the scope of the invention.

EXAMPLE

Provided below is an example of a method for forming a nanostructured surface according to an embodiment of the invention:

Step 1: Sample preparation: A silicon wafer or a glass slide is cleaned and then coated with a thin layer of titanium (10 nm) followed by a layer of gold (5-10 nm) and a thick layer of aluminum (1.5 μm) using an e-beam evaporator. The Al layer is then electropolished in a 9:1 ethanol to water solution to remove to remove any oxide layer prior to anodization. See FIG. 5A.

Step 2: Anodization: Anodization in 0.3 M oxalic acid at 5° C. at 40 V is performed until it reaches the gold layer through the monitoring of the anodization current. See FIG. 5B.

Step 3: Electrodeposition: Silver nanopillars are formed through electrodeposition into the nanopores in a silver potassium cyanide bath at 5 mA/cm$^2$ for 50 s. See FIG. 5C.

Step 4: Alumina removal: The alumina template is removed by dipping in 2.0M NaOH solution for about 20 minutes. See FIG. 5D.

Step 5: Micro patterning: Photoresist 1818 (positive photoresist) is spin coated on the sample and then exposed to UV light through a micro pattern mask. See FIGS. 6A and 6B.

Step 6: Photoresist development: The micro pattern is developed using MF 319 developer solution. See FIG. 6C.

Step 7: Etching of Gold and Titanium: The unmasked gold layer is etched at room temperature in solution containing KI: $I_2H_2O$ (4 g:1 g:40 g) and titanium layer is etched in solution containing $H_2O:HF:H_2O_2$ (20:1:1). See FIG. 7A.

Step 8: Photoresist removal: The masking photoresist is chemically stripped using photoresist remover, leading to a SERS substrate with micro islands incorporated with standing nanopillars. See FIG. 7B.

In the drawings and specification, there have been disclosed typical embodiments of the invention and, although specific terms are employed, they are used in a generic and descriptive sense only and not for purposes of limitation, the scope of the invention being set forth in the following claims.

The invention claimed is:

1. A nanostructured surface for detecting an analyte comprising:
   a glass or silicon substrate;
   an array of metallic nanopillar islands on the glass or silicon substrate, wherein each metallic nanopillar island comprises a metal base layer on the glass or silicon substrate and a plurality of metallic nanopillars on the metal base layer, and wherein portions of the glass or silicon substrate between adjacent metallic nanopillar islands are free of the metal base layer wherein the metallic nanopillars have an aspect ratio in a range of about 5:1 to about 500:1; and
   a driver circuit in electrical contact with at least one metallic nanopillar island through the metal base layer connected to the driver circuit through a metallic bridge or an electrical lead on or through the substrate, wherein the driver circuit generates an electrical potential sufficient to cause at least a portion of the metallic nanopillars of the at least one metallic nanopillar island to shift position.

2. The nanostructured surface of claim 1, wherein the metallic nanopillar islands are circular.

3. The nanostructured surface of claim 1, wherein the array of nanopillar islands has an inter-island distance in a range of about 100 nm to about 1 mm; and wherein each metallic nanopillar island comprises a hexagonal array of metallic nanopillars with an inter-pillar distance in a range of about 1 nm to about 500 nm.

4. The nanostructured surface of claim 3, wherein a width of the metallic nanopillars is in a range of about 10 nm to about 500 nm.

5. The nanostructured surface of claim 1, wherein the metal base layer of each metallic nanopillar island comprises a layer of titanium and/or a layer of gold, and wherein the plurality of metallic nanopillars comprises silver and/or gold.

6. The nanostructured surface of claim 1, wherein the metal base layer of each metallic nanopillar island comprises a layer of titanium and/or a layer of gold, and wherein the plurality of nanopillars comprises at least one metal selected from the group consisting of aluminum, silver, gold, copper, titanium and tantalum.

7. The nanostructured surface of claim 1, further comprising at least one probe molecule immobilized on at least one metallic nanopillar island.

8. The nanostructured surface of claim 1, wherein two or more metallic nanopillar islands are electrically coupled.

9. An apparatus for detecting an analyte by Surface Enhanced Raman Spectroscopy comprising:

(i) a nanostructured surface comprising
a glass or silicon substrate;
an array of metallic nanopillar islands on the glass or silicon substrate, wherein each metallic nanopillar island comprises a metal base layer on the glass or silicon substrate and a plurality of metallic nanopillars on the metal base layer, and wherein portions of the glass or silicon substrate between adjacent metallic nanopillar islands are free of the metal base layer wherein the metallic nanopillars have an aspect ratio in a range of about 5:1 to about 500:1; and
a driver circuit in electrical contact with at least one metallic nanopillar island through the metal base layer connected to the driver circuit through a metallic bridge or an electrical lead on or through the substrate, wherein the driver circuit generates an electrical potential sufficient to cause at least a bundled portion of the metallic nanopillars of the at least one metallic nanopillar island to open;

(ii) a radiation source, the radiation source operable to provide incident radiation to the nanostructured surface; and (iii) a detector, the detector positioned to receive radiation scattered from at least one analyte bound to the nanostructured surface, the scattered radiation being used to detect the analyte.

10. The apparatus of claim 9, wherein the array of metallic nanopillar islands has an inter-island distance in a range of about 100 nm to about 1 mm, and wherein each metallic nanopillar island comprises a hexagonal array of metallic nanopillars with an inter-pillar distance in a range of about 10 nm to about 500 nm.

11. The apparatus of claim 9, wherein the at least one analyte is bound to at least one metallic nanopillar island.

12. The apparatus of claim 9, wherein the incident radiation has a wavelength that excites surface plasmons within a metal in the metal base layer and/or the metallic nanopillars.

13. The apparatus of claim 9, further comprising
a stage, wherein the nanostructured surface is on the stage; and
a controller, wherein the controller is connected to the stage and is configured to translate and/or rotate the stage.

14. A method of detecting at least one analyte and/or a biological or chemical binding event by electrical double layer (EDL) capacitance comprising:

(i) providing at least one analyte to an apparatus comprising
(a) a nanostructured surface comprising
a glass or silicon substrate;
an array of metallic nanopillar islands on the glass or silicon substrate, wherein each metallic nanopillar island comprises a metal base layer on the glass or silicon substrate and a plurality of metallic nanopillars on the metal base layer, and wherein portions of the glass or silicon substrate between adjacent metallic nanopillar islands are free of the metal base layers wherein the metallic nanopillars have an aspect ratio in a range of about 5:1 to about 500:1; and
a driver circuit in electrical contact with at least one metallic nanopillar island through the metal base layer connected to the driver circuit through a metallic bridge or an electrical lead on or through the substrate, wherein the driver circuit generates an electrical potential sufficient to cause at least a portion of the metallic nanopillars of the at least one metallic nanopillar island to shift position;
(b) an electrolyte in contact with at least one metallic nanopillar island; and
(c) a reference electrode in electrical contact with the electrolyte;

(ii) measuring capacitances between at least one metallic nanopillar island and the reference electrode; and (iii) correlating the measured capacitances to detect whether the at least one analyte binds to the at least one of metallic nanopillar island.

15. The method of claim 14, wherein the array of metallic nanopillar islands has an inter-island distance in a range of about 100 nm to about 1 mm, and wherein each metallic nanopillar island comprises a hexagonal array of metallic nanopillars with an inter-pillar distance in a range of about 10 nm to about 500 nm.

16. The method of claim 14, further comprising at least one probe molecule immobilized on the at least one metallic nanopillar island and wherein the measured capacitances are correlated to detect whether the at least one analyte binds to the at least one probe molecule.

17. The method of claim 16, wherein the at least one probe molecule and the at least one analyte are nucleic acids that bind by hybridization.

18. The method of claim 16, wherein the at least one analyte and/or the at least one probe molecule is a peptide, protein, virus, nucleotide, cell, bacterium, conjugated nanoparticles and/or lipid bilayer.

* * * * *